United States Patent
Laviola

(10) Patent No.: US 11,707,244 B2
(45) Date of Patent: Jul. 25, 2023

(54) TECHNIQUES FOR BREAST IMAGING PATIENT MOTION ARTIFACT COMPENSATION

(71) Applicant: HOLOGIC, INC., Marlborough, MA (US)

(72) Inventor: John Laviola, Orange, CT (US)

(73) Assignee: Hologic, Inc., Marlborough, MA (US)

(*) Notice: Subject to any disclaimer, the term of this patent is extended or adjusted under 35 U.S.C. 154(b) by 0 days.

(21) Appl. No.: 16/639,226

(22) PCT Filed: Aug. 16, 2018

(86) PCT No.: PCT/IB2018/056208
§ 371 (c)(1),
(2) Date: Feb. 14, 2020

(87) PCT Pub. No.: WO2019/035064
PCT Pub. Date: Feb. 21, 2019

(65) Prior Publication Data
US 2020/0196971 A1     Jun. 25, 2020

Related U.S. Application Data

(60) Provisional application No. 62/546,167, filed on Aug. 16, 2017.

(51) Int. Cl.
*A61B 6/00* (2006.01)
*A61B 6/04* (2006.01)
(Continued)

(52) U.S. Cl.
CPC .............. *A61B 6/527* (2013.01); *A61B 6/035* (2013.01); *A61B 6/0414* (2013.01); *A61B 6/461* (2013.01);
(Continued)

(58) Field of Classification Search
CPC ............ A61B 6/527; A61B 6/502; G06T 7/20
See application file for complete search history.

(56) References Cited

U.S. PATENT DOCUMENTS 3,971,950 A    7/1976   Evans et al.
4,496,557 A    1/1985   Malen
(Continued)

FOREIGN PATENT DOCUMENTS

AU    2008201638    5/2008
CN    1586399       3/2005
(Continued)

OTHER PUBLICATIONS

Digital Clinical Reports, Tomosynthesis (GE Brochure 98-5493, Nov. 1998), 8 pgs.
(Continued)

*Primary Examiner* — Angela M Hoffa
*Assistant Examiner* — Younhee Choi
(74) *Attorney, Agent, or Firm* — Merchant & Gould P.C.

(57) ABSTRACT

An imaging system may include an imaging detector to capture an image of human tissue and a compression paddle situated apart from the imaging detector to compress the human tissue between the compression paddle and the imaging detector. A force sensor may generate a force signal indicating a measure of force applied superior to the human tissue. A movement detection circuit may filter a movement signal from the force signal indicating a measure of movement of the compressed human tissue. A movement analysis module may determine that the movement signal is beyond a movement threshold. An image correction module to perform a corrective action based upon the determination that the movement signal is beyond a movement threshold.

17 Claims, 16 Drawing Sheets

(51) Int. Cl.
   *A61B 6/03*   (2006.01)
   *A61B 8/08*   (2006.01)
   *A61B 8/13*   (2006.01)
   *A61B 8/00*   (2006.01)
   *A61B 6/02*   (2006.01)

(52) U.S. Cl.
   CPC .............. *A61B 6/463* (2013.01); *A61B 6/465* (2013.01); *A61B 6/502* (2013.01); *A61B 6/5258* (2013.01); *A61B 6/54* (2013.01); *A61B 6/025* (2013.01); *A61B 6/566* (2013.01); *A61B 8/0825* (2013.01); *A61B 8/13* (2013.01); *A61B 8/4254* (2013.01)

(56) References Cited

U.S. PATENT DOCUMENTS

| | | |
|---|---|---|
| 4,943,986 A | 7/1990 | Barbarisi |
| 5,051,904 A | 9/1991 | Griffith |
| 5,107,255 A | 4/1992 | Shiraishi |
| 5,199,056 A | 3/1993 | Darrah |
| 5,359,637 A | 10/1994 | Webber |
| 5,398,272 A | 3/1995 | Bouscary et al. |
| 5,506,877 A | 4/1996 | Niklason |
| 5,553,111 A | 9/1996 | Moore et al. |
| D376,012 S | 11/1996 | Hixson, Sr. |
| 5,706,327 A | 1/1998 | Adamkowski |
| 6,289,235 B1 | 9/2001 | Webber |
| 6,647,092 B2 | 11/2003 | Eberhard |
| 7,123,684 B2 | 10/2006 | Jing et al. |
| 7,203,348 B1 | 4/2007 | Karrsemeijer |
| 7,245,694 B2 | 7/2007 | Jing et al. |
| 7,430,272 B2 | 9/2008 | Jing et al. |
| 7,583,786 B2 | 9/2009 | Jing et al. |
| 7,831,296 B2 | 11/2010 | Defreitas |
| 7,869,563 B2 | 1/2011 | Defreitas et al. |
| 8,175,219 B2 | 5/2012 | DeFreitas et al. |
| 8,787,522 B2 | 7/2014 | Smith et al. |
| 9,050,009 B2 | 6/2015 | Den Heeten |
| 9,226,718 B1 | 1/2016 | Baxley |
| 9,332,947 B2 | 5/2016 | DeFreitas et al. |
| 9,498,180 B2 | 11/2016 | Ren et al. |
| 9,743,997 B2 | 8/2017 | Grimbergen |
| 9,782,135 B2 | 10/2017 | Stango et al. |
| 9,826,950 B2 | 11/2017 | Den Heeten |
| 10,603,002 B2 | 3/2020 | Stango |
| 10,888,292 B2 | 1/2021 | Stango |
| 2001/0038861 A1 | 11/2001 | Hsu |
| 2002/0061090 A1 | 5/2002 | Lindstrom |
| 2003/0007597 A1 | 1/2003 | Higgins et al. |
| 2004/0066873 A1 | 4/2004 | Eberhard |
| 2004/0066884 A1 | 4/2004 | Claus |
| 2004/0066904 A1 | 4/2004 | Eberhard |
| 2004/0218727 A1 | 11/2004 | Shoenfeld |
| 2005/0008117 A1 | 1/2005 | Livingston |
| 2005/0063509 A1 | 3/2005 | DeFreitas et al. |
| 2005/0113681 A1 | 5/2005 | DeFreitas et al. |
| 2005/0113683 A1 | 5/2005 | Lokhandwalla et al. |
| 2006/0165215 A1 | 7/2006 | Galkin |
| 2007/0223652 A1 | 9/2007 | Galkin |
| 2007/0242794 A1 | 10/2007 | Stanton |
| 2007/0280412 A1 | 12/2007 | Defreitas et al. |
| 2008/0043904 A1 | 2/2008 | Hoernig |
| 2008/0080668 A1 | 4/2008 | Kashiwagi |
| 2008/0087830 A1 | 4/2008 | Kashiwagi |
| 2008/0242979 A1 | 10/2008 | Fischer et al. |
| 2009/0262887 A1 | 10/2009 | Iordache et al. |
| 2009/0268865 A1 | 10/2009 | Ren |
| 2009/0324049 A1 | 12/2009 | Kontos et al. |
| 2010/0046698 A1 | 2/2010 | Lebovic et al. |
| 2010/0049093 A1 | 2/2010 | Galkin |
| 2010/0111249 A1 | 5/2010 | Mertelmeir et al. |
| 2011/0058724 A1 | 3/2011 | Claus |
| 2011/0087098 A1 | 4/2011 | Fischer et al. |
| 2011/0257919 A1 | 5/2011 | Reiner |
| 2012/0033868 A1* | 2/2012 | Ren ........................ A61B 6/5223 382/131 |
| 2012/0051522 A1* | 3/2012 | Nishino ................ A61B 6/4007 378/108 |
| 2012/0114095 A1 | 5/2012 | Smith et al. |
| 2012/0277625 A1 | 11/2012 | Nakayama |
| 2013/0012837 A1* | 1/2013 | Kogure .................. A61B 5/113 600/595 |
| 2013/0028499 A1* | 1/2013 | Tsujii .................... A61B 6/5258 382/132 |
| 2013/0272493 A1 | 10/2013 | Otokuni |
| 2014/0107493 A1* | 4/2014 | Yuen ...................... A61B 5/6898 600/473 |
| 2014/0296701 A1 | 10/2014 | Hancu et al. |
| 2014/0328458 A1 | 11/2014 | Erhard et al. |
| 2014/0378816 A1* | 12/2014 | Oh ......................... G01R 33/283 600/409 |
| 2015/0272682 A1 | 10/2015 | Sheng |
| 2015/0282770 A1 | 10/2015 | Klanian et al. |
| 2016/0066875 A1 | 3/2016 | Jacob et al. |
| 2016/0081633 A1 | 3/2016 | Stango et al. |
| 2016/0183889 A1* | 6/2016 | Matsuura ................ A61B 6/54 378/37 |
| 2016/0242707 A1 | 8/2016 | Defreitas et al. |
| 2017/0251991 A1 | 9/2017 | Wang |
| 2017/0340303 A1 | 11/2017 | Stango |
| 2018/0165840 A1 | 6/2018 | Bernard |
| 2018/0184999 A1 | 7/2018 | Davis |
| 2020/0069274 A1 | 3/2020 | Stango |
| 2020/0178926 A1 | 6/2020 | Kshirsagar |
| 2020/0359974 A1 | 11/2020 | DeFreitas |
| 2020/0359975 A1 | 11/2020 | Banks |
| 2020/0390405 A1 | 12/2020 | DeFreitas |
| 2021/0015435 A1 | 1/2021 | DeFreitas |
| 2021/0113169 A1 | 4/2021 | Stango |
| 2021/0228165 A1 | 7/2021 | Defreitas |
| 2022/0087627 A1 | 3/2022 | Stango |

FOREIGN PATENT DOCUMENTS

| | | | |
|---|---|---|---|
| CN | 102196772 | 9/2011 | |
| CN | 102448375 | 5/2012 | |
| CN | 102781328 | 11/2012 | |
| CN | 103281961 | 9/2013 | |
| CN | 104066374 | 9/2014 | |
| CN | 105286904 A | 2/2016 | |
| CN | 105637562 | 6/2016 | |
| CN | 105769236 | 7/2016 | |
| CN | 112004473 | 11/2020 | |
| CN | 115348838 | 11/2022 | |
| EP | 955886 | 11/1999 | |
| EP | 2341832 B1 | 7/2014 | |
| EP | 2943125 B1 | 9/2018 | |
| GB | 2545641 A * | 6/2017 | ........... G06T 7/0012 |
| JP | S53-103672 | 8/1978 | |
| JP | H03-86154 | 4/1991 | |
| JP | 2003-525681 | 9/2003 | |
| JP | 2005-523043 | 8/2005 | |
| JP | 2009-219656 | 10/2009 | |
| JP | 8-215172 | 3/2010 | |
| JP | 2011-072667 | 4/2011 | |
| JP | 2011-206436 | 10/2011 | |
| JP | 2011-224351 | 11/2011 | |
| JP | 2011-250842 | 12/2011 | |
| JP | 2012-125536 | 7/2012 | |
| JP | 2012-170718 | 9/2012 | |
| JP | 2012-228404 | 11/2012 | |
| JP | 2013017491 A * | 1/2013 | ........... A61B 6/0421 |
| JP | 2014-068884 | 4/2014 | |
| JP | 2014-068885 | 4/2014 | |
| JP | 2015-027382 | 2/2015 | |
| JP | 2016-022061 | 2/2016 | |
| JP | 2016-517740 | 6/2016 | |
| KR | 10-2011-0089446 | 8/2011 | |
| KR | 10-2014-0058066 | 5/2014 | |
| NL | 2020910 B1 | 11/2019 | |
| WO | 2006/050466 | 5/2006 | |
| WO | 2010/028208 | 3/2010 | |

(56) References Cited

FOREIGN PATENT DOCUMENTS

| WO | 2010/102087 | 9/2010 |
| WO | 2011/058730 | 5/2011 |
| WO | 2014059366 | 4/2014 |
| WO | 2014/074602 | 5/2014 |
| WO | 2014/176445 A2 | 10/2014 |
| WO | 2015/054518 | 4/2015 |
| WO | 2016/073445 | 5/2016 |
| WO | 2018/067005 | 4/2018 |
| WO | 2018/089118 | 5/2018 |
| WO | 2018/170265 | 9/2018 |
| WO | 2019/004821 | 1/2019 |
| WO | 2019/088826 | 5/2019 |
| WO | 20190227042 | 11/2019 |
| WO | 20190227044 | 11/2019 |

OTHER PUBLICATIONS

European Extended Search Report in Application 15857678.5, dated Jun. 26, 2018, 8 pages.

Grant, D.G., "Tomosynthesis: a three-dimensional imaging technique", IEEE Trans. Biomed. Engineering, vol. BME-19, #1, (Jan. 1972), pp. 20-28.

PCT International Preliminary Report on Patentability in International Application PCT/IB2018/056208, dated Feb. 27, 2020, 10 pages.

PCT International Preliminary Report on Patentability in International Application PCT/US2015/058782, dated May 18, 2017, 10 pgs.

PCT International Preliminary Report on Patentability in international Application PCT/US2017/053311, dated May 14, 2019, 14 pgs.

PCT International Preliminary Report on Patentability in International Application PCT/US2018/046304, dated Feb. 11, 2020, 14 pgs.

PCT International Preliminary Report on Patentability in International Application PCT/US2018/046312, dated Feb. 11, 2020, 12 pgs.

PCT International Search Report and Written Opinion of the International Searching Authority for corresponding International Patent Application No. PCT/US2015/058782 dated Feb. 17, 2016, 14 pgs.

PCT International Search Report and Written Opinion of the International Searching Authority for International Patent Application No. PCT/US2017/053311 dated Mar. 6, 2018, 21 pages.

PCT International Search Report and Written Opinion of the International Searching Authority for International Patent Application No. PCT/US2018/046304 dated Dec. 11, 2018, 18 pages.

PCT International Search Report and Written Opinion of the International Searching Authority for International Patent Application No. PCT/US2018/046312 dated Dec. 11, 2018, 14 pages.

U.S. Appl. No. 60/628,516 entitled "Matching geometry generation and display of mammograms and tomosynthesis images", filed Nov. 15, 2004, 20 pgs.

International Search Report and Written Opinion of the International Searching Authority for International Patent Application No. PCT/IB2018/056208 dated Nov. 13, 2018, 12 pages.

PCT Invitation to Pay additional Fees, in Application PCT/US2021/013716, dated May 6, 2021, 17 pages.

PCT International Search Report and Written Opinion in International Application PCT/US2021/013716, dated Jun. 28, 2021, 24 pages.

European Extended Search Report in Application 18843788.3, dated Mar. 29, 2021, 16 pages.

European Communication and Search Report in Application 18847121.3, dated Apr. 8, 2021, 5 pages.

European Extended Search Report in Application 18843590.3, dated Mar. 25, 2021, 9 pages.

Japanese Rejection in Application 2019-521374, dated Jul. 26, 2021, 5 pages.

European Extended Search Report in Application 22183201.7, dated Dec. 5, 2022, 7 pages.

* cited by examiner

TECHNIQUES FOR BREAST IMAGING PATIENT MOTION ARTIFACT COMPENSATION

RELATED APPLICATIONS

This application is a National Stage Application of PCT/IB2018/056208, filed on Aug. 16, 2018, which claims priority to: U.S. Provisional Patent Application Ser. No. 62/546,167, entitled "Techniques for Breast Imaging Patient Motion Artifact Compensation" and filed on Aug. 16, 2017. The contents of the aforementioned applications are incorporated herein by reference. To the extent appropriate, a claim of priority is made to each of the above disclosed applications.

FIELD OF THE DISCLOSURE

The disclosure generally relates to quality assurance of patient imaging, and more particularly to improving detection of movement and correction of motion artifacts, such as it relates to mammography or tomosynthesis image acquisition.

BACKGROUND

Preventing movement of subject tissue, and in particular breast tissue, is important when performing radiation-based imaging of a patient for a variety of reasons. First, some imaging procedures last for a non-trivial period of time, and movement during a portion of the procedure may negatively impact image quality. Specifically, patient motion may cause anatomical distortions or artifacts, which can be exaggerated during longer exposure times. Second, it is desirable to minimize a patient's total exposure to radiation during a procedure and, thus, subsequent imaging to obtain proper image quality is not ideal. Third, due to regulations in many jurisdictions, subsequent imaging used solely to correct image quality may be counted against a practitioner or organization, and frequent re-imaging may result in revocation of a license and/or accreditation. Fourth, poor quality images due to excess movement may require a patient to make subsequent visits to an imaging center, placing additional burden on the patient and the healthcare system itself, including the imaging center and payer.

SUMMARY

The following presents a simplified summary in order to provide a basic understanding of some novel embodiments described herein. This summary is not an extensive overview, and it is not intended to identify key/critical elements or to delineate the scope thereof. Its sole purpose is to present some concepts in a simplified form as a prelude to the more detailed description that is presented later.

Techniques for detecting and/or otherwise notifying a patient detected motion and modifying the imaging protocol during breast imaging are described. As described above, preventing movement breast tissue, is important when performing radiation-based imaging of a patient for a variety of reasons including improving image quality, improving patient experience, reducing exposure and avoiding repeat imaging. For at least these reasons, there is a need for improved techniques, which may be automated or semi-automated, for detection of movement during an imaging procedure, for corrective actions during and after the procedure when movement has been detected, and for minimizing the amount of radiation exposure to patients in a workflow efficient manner.

An imaging system as described herein may include an imaging detector to capture an image of human tissue, such as breast tissue, and a compression paddle situated apart from the imaging detector to compress the human tissue between the compression paddle and the imaging detector. One or more sensors may be included, in one embodiment a force sensor may generate a force signal indicating a measure of force applied to the human tissue. A movement detection circuit may filter a movement signal from the force signal indicating a measure of movement of the compressed human tissue. A movement analysis module may determine that the movement signal is beyond a movement threshold. An image correction module to perform a corrective action based upon the determination that the movement signal is beyond a movement threshold. Other embodiments are described and claimed.

The force sensor described herein is typical to most modern mammography systems where breast compression force is incorporated. The force sensor helps to prevent excessive compression of the patient's breast which can cause pain and other undesirable effects. The embodiments as described and claimed relate to the output of the force sensor, representative of a force level, which may be filtered or converted by one or more circuits or modules described herein into a value that indicates movement. This movement signal, when compared to other measurements over time, may indicate movement of the patient undergoing an imaging procedure.

In addition or in the alternative, other sensors may be used. For example, one or more ultrasound sensors, optical and/or infrared sensors may be used. In some examples, the sensors may be located either in a grid on the compression paddle. In other examples, the sensors may be located on the periphery of the paddle. The sensors may capture spatial data information from the compression of the breast. The special information may be used to create motion maps and/or contact maps. The motion map information can be used to create a correction map. The correction map information may be used as input to the image correction algorithm which corrects the tomosynthesys images. In the examples where a contact map is created based on the spatial information, the contact map can be used to create compression contours, which can be used as an input to the compression adequacy analysis and recommend a corrective action.

Some software based techniques for detecting motion during an imaging procedure have been previously described. For example, one method of detecting patient motion includes detecting from a series of images displacement of an edge line such as the skin line of the breast, an implant edge, or some other internal edge. This skin line detection process is disclosed in U.S. Pat. No. 9,498,180, titled SYSTEM AND METHOD FOR DETECTING PATIENT MOTION DURING TOMOSYNTHESIS SCANS, which is incorporated by reference herein (hereafter the '180 Patent).

However, unlike software based and image artifact based motion detection, detection of motion based on hardware sensors gives an objective measure of patient motion to add to the assessment of motion. The independent, hardware based, detection using the information from one or more sensors allows for greater accuracy. In addition, because the mammography system already includes the force sensor, this method of patient motion is more cost effective than the alternative image based detection when force sensor detection is used. In addition, different types of motion may be detected and different compensation actions may be taken. For example, if motion with regular movement interval is detected, such as breathing or heartbeat, image capture may be synchronized with the motion. In a different example, if irregular movement is detected, such as patient adjusting position, the image capture may be delayed. Such nuanced and continued detection may not be possible if the detection is based on image processing alone.

To the accomplishment of the foregoing and related ends, certain illustrative aspects are described herein in connection with the following description and the annexed drawings. These aspects are indicative of the various ways in which the principles disclosed herein can be practiced and all aspects and equivalents thereof are intended to be within the scope of the claimed subject matter. Other advantages and novel features will become apparent from the following detailed description when considered in conjunction with the drawings.

DETAILED DESCRIPTION

Figure 1:
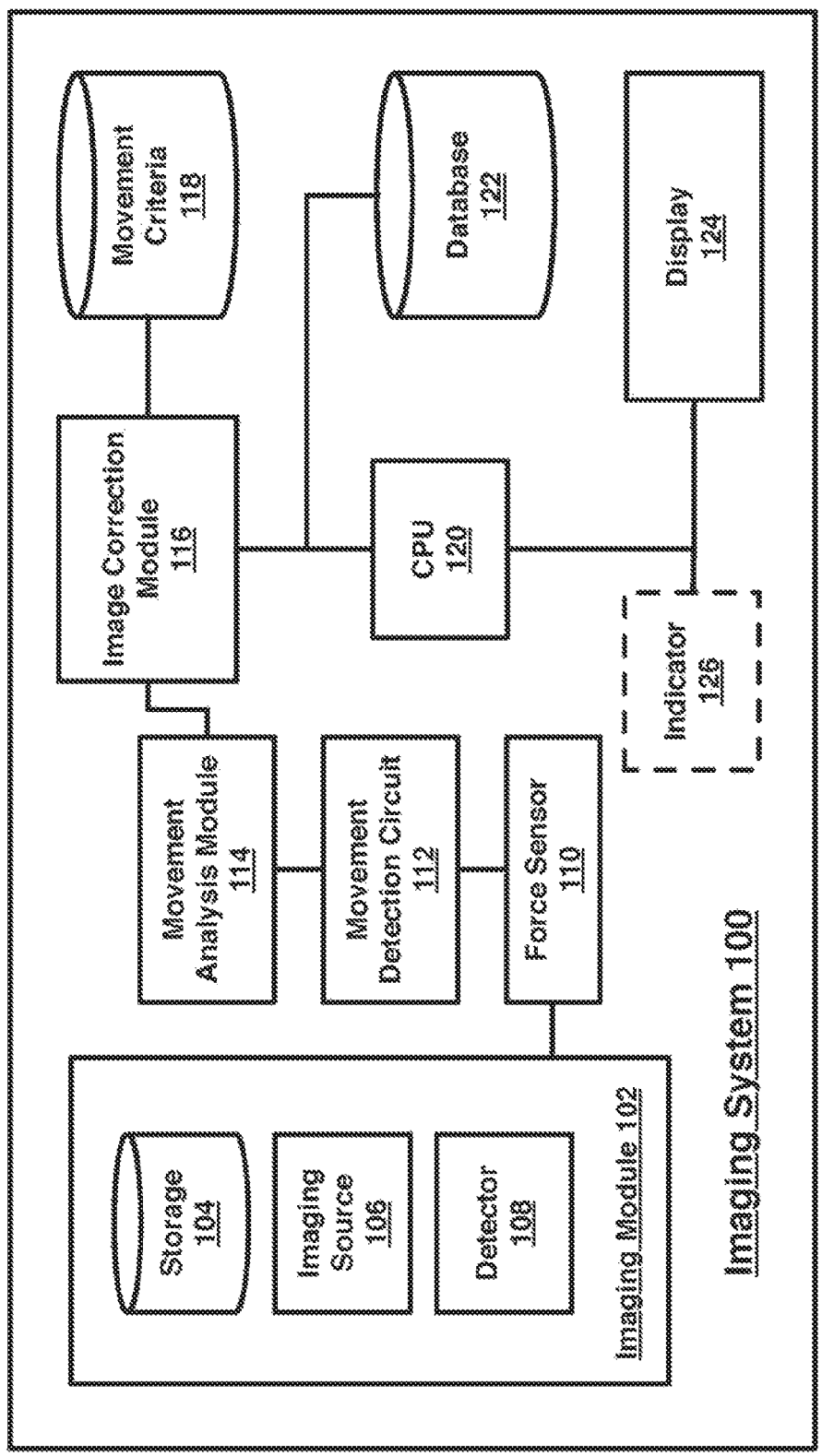
FIG. 1 illustrates an embodiment of an imaging system.

Techniques for breast imaging patient motion compensation are described. An imaging system may include an imaging detector to capture an image of human tissue, such as breast tissue or other soft tissue, and a compression paddle situated apart from the imaging detector to compress the human tissue between the compression paddle and the imaging detector. In one embodiment, a force sensor may generate a force signal indicating a measure of force applied to the human tissue. A movement detection circuit may filter a movement signal from the force signal indicating a measure of movement of the compressed human tissue. A movement analysis module may determine that the movement signal is beyond a movement threshold. An image correction module to perform a corrective action based upon the determination that the movement signal is beyond a movement threshold. In another embodiment, other types of sensors may be used which may be disposed in a grid or around the periphery of the compression paddle.

As used herein, corrective actions may include actions to correct an image, generate an image while minimizing motion artifacts, generate an audio or visual indication that motion has been detected, and/or other actions described below in response to detection of motion during a procedure. By way of example and not limitation, corrective actions may include the determination and display of a movement score on a display device, display of an alert on a display device indicating that a movement threshold has been exceeded, triggering a visual indicator of the imaging system, terminating or modifying an imaging sequence or imaging protocol or image acquisition, delaying capture of the image of human tissue until the movement threshold is no longer exceeded, and/or synchronizing an image capture with repetitive movement. A movement score for all images taken by a particular technologist may be combined to create a positioning score for the technologist. The movement scores may be compared to other technologists in a facility or in other facilities. The technologist score may be compared to a threshold to determine compliance. A facility score may be compared to other facilities and compared to a threshold score to determine compliance. A report may be generated showing positioning scores for the technologist, the facility and compliance over time. A retrospective and prospective approach will allow the facility to identify the root-cause for why the positioning, noise, artifacts, compression etc. at the physician level could occur. A particular technician can be identified with this approach to understand his/her behavior to improve their ability to take their image. Other embodiments are described and claimed.

With general reference to notations and nomenclature used herein, the detailed descriptions which follow may be presented in terms of program procedures executed on a computer or network of computers. These procedural descriptions and representations are used by those skilled in the art to most effectively convey the substance of their work to others skilled in the art.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein which form part of one or more embodiments. Rather, the operations are machine operations. Useful machines for performing operations of various embodiments include general purpose digital computers or similar devices.

Various embodiments also relate to apparatus or systems for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove convenient to construct more specialized apparatus to perform the required method steps. The required structure for a variety of these machines will appear from the description given.

FIG. 1 illustrates a block diagram for an imaging system 100. In one embodiment, the imaging system 100 may comprise one or more components. Although the imaging system 100 shown in FIG. 1 has a limited number of elements in a certain topology, it may be appreciated that the imaging system 100 may include more or less elements in alternate topologies as desired for a given implementation. The imaging system 100 may include a plurality of modules, including imaging module 102, movement analysis module 114, and image correction module 116, which may each include one or more processing units, storage units, network interfaces, or other hardware and software elements described in more detail herein. In some embodiments, these modules may be included within a single imaging device, utilizing shared CPU 120. In other embodiments, one or more modules may be part of a distributed architecture, an example of which is described with respect to FIG. 11.

In an embodiment, each module of imaging system 100 may comprise without limitation an imaging system, mobile computing device, a smart phone, or a desktop computer, or other devices described herein. In various embodiments, imaging system 100 may comprise or implement multiple components or modules. As used herein the terms "component" and "module" are intended to refer to computer-related entities, comprising either hardware, a combination of hardware and software, software, or software in execution. For example, a component and/or module can be implemented as a process running on a processor, such as CPU 120, a hard disk drive, multiple storage drives (of optical and/or magnetic storage medium), an object, an executable, a thread of execution, a program, and/or a computer. By way of illustration, both an application running on a server and the server can be a component and/or module. One or more components and/or modules can reside within a process and/or thread of execution, and a component and/or module can be localized on one computer and/or distributed between two or more computers as desired for a given implementation. The embodiments are not limited in this context.

The various devices within system 100, and components and/or modules within a device of system 100, may be communicatively coupled via various types of communications media as indicated by various lines or arrows. In various embodiments, the various modules and storages of system 100 may be organized as a distributed system. A distributed system typically comprises multiple autonomous computers that communicate through a computer network. It is worthy to note that although some embodiments may utilize a distributed system when describing various enhanced techniques for data retrieval, it may be appreciated that the enhanced techniques for data retrieval may be implemented by a single computing device as well. The embodiments are not limited in this context.

In an embodiment, imaging module 102 may include an imaging source 106 and a detector 108, which may be used to perform breast imaging (2D, tomosynthesis, computed tomography, ultrasound or any combination thereof), and may be an x-ray source and detector in some examples. In other examples, imaging source 106 and detector 108 may be other types of imaging sources and sensors, respectively. For example, in some embodiments imaging module 102 may be configured to perform breast imaging, such as x-ray mammography, tomosynthesis, computed tomography, and/or ultrasound. Tomosynthesis is a method for performing high-resolution limited-angle tomography at radiographic dose levels. While mammography is used as an exemplary embodiment through the description, it can be appreciated that the techniques described herein may be applicable to other procedures in which imaging of human tissue susceptible to movement may occur.

Imaging source 106 may be configured to expose human tissue, such as breast tissue, to x-rays, which may be detected by detector 108. Detector 108 may be configured to respond to the influence of incident x-rays over a wide range. Detector 108 may be configured to absorb x-rays, produce an electronic signal, digitize the signal, and store the results in one of storage 104 and/or database 122. The output image may be saved as a two-dimensional matrix, where each element represents the x-ray transmission corresponding to a path through the breast tissue. Three-dimensional images and matrices may be generated in some embodiments, depending on the imaging modality, such as tomosynthesis, computed tomography, and the like. The image may be digitally processed such that when it is displayed on a display device or printed on laser film, it will illustrate the key features required for diagnosis. Such diagnostic images may be stored in storage 104 so that they may be viewed on a user interface of display 124.

In an embodiment, images may also be archived in image database 122. In this manner, patient records may be maintained and past images may be used to evaluate detected movement when compared to new images. In an exemplary embodiment, an image correction module, described herein, may refer to archived images containing common elements (e.g., still calcification for the same tissue of the same patient) and compare to a current image (which may include blurry calcifications for the same tissue of the same patient). Such as analysis, combined with the techniques described herein, may be used to detect and/or correct motion artifacts within an image.

Figure 2:
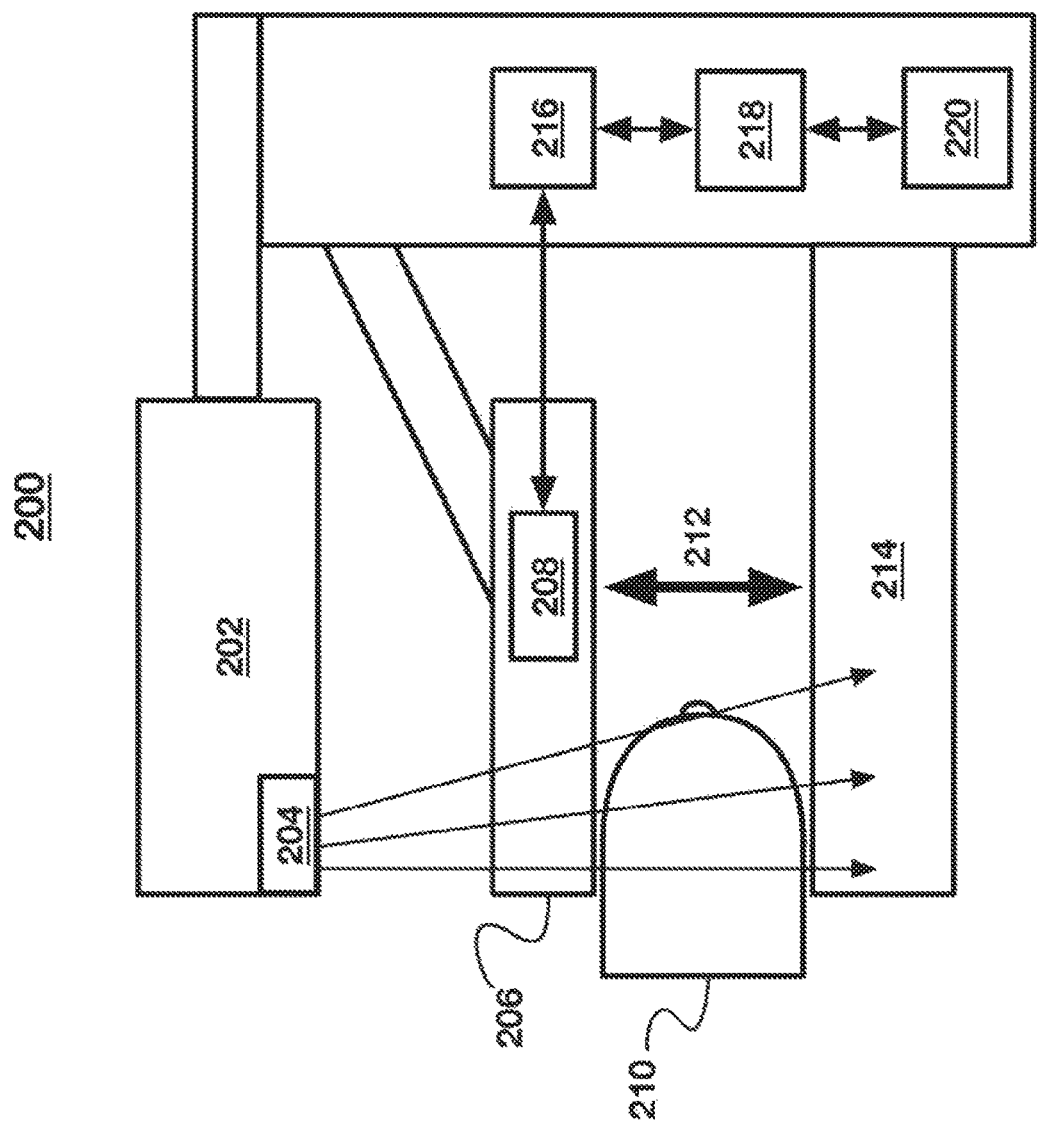
FIG. 2 illustrates an embodiment of an imaging system.
Figure 3:
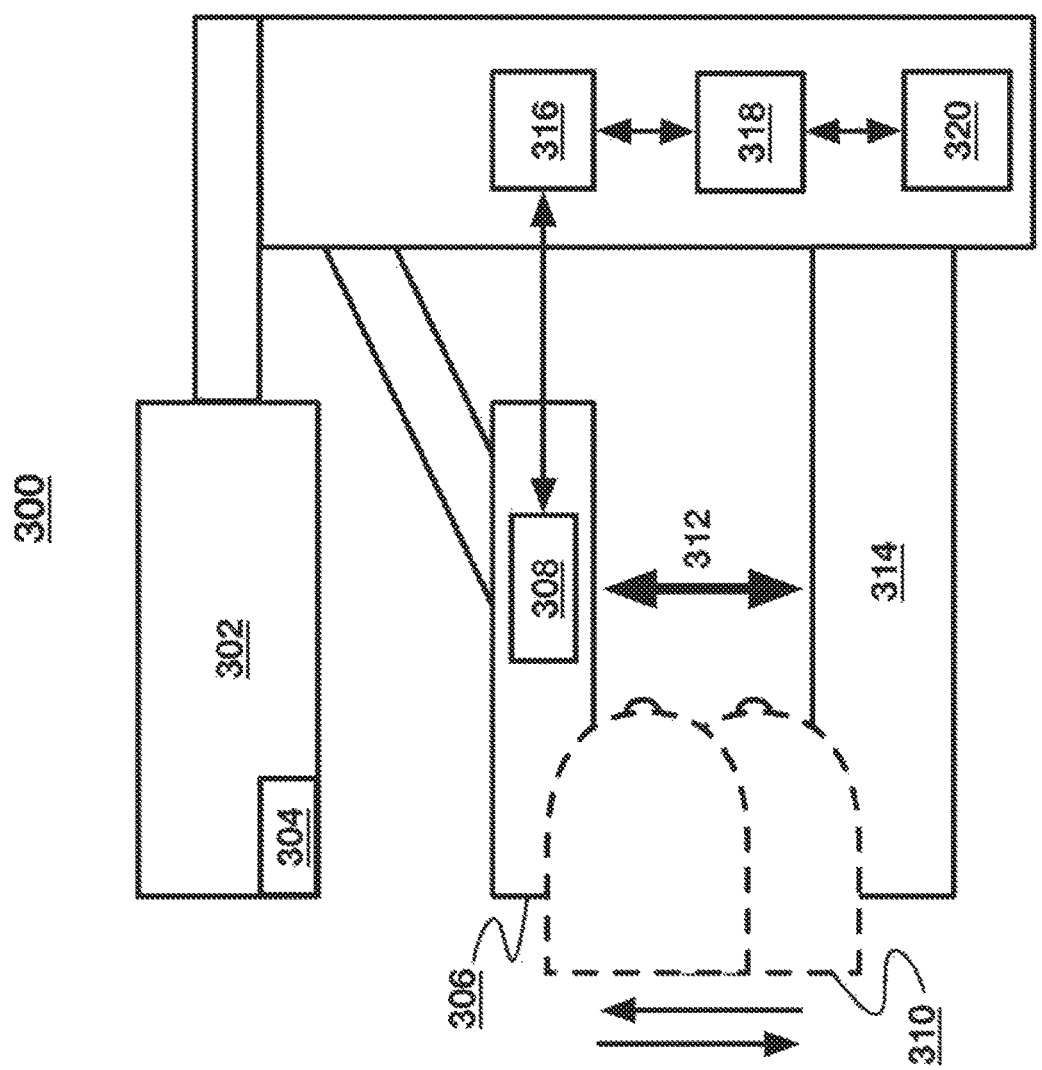
FIG. 3 illustrates an embodiment of an imaging system.

Imaging system 100 may include a force sensor 110, which may be contained within a compression paddle of imaging system 100 (not shown in FIG. 1, illustrated in FIGS. 2 and 3). Force sensor 110 may include a strain gauge, piezoelectric sensor, load cell, or other sensor capable of measuring the force applied to human tissue compressed between a compression paddle and an opposite detector plane. In some embodiments, force sensor 110 may include an analog filter, gain circuits for signal conditioning, and/or an analog-to-digital converter for signal capture. The output of force sensor 110 may be an electrical signal representative of a force level. The force level may represent a measurement of force applied superior to the breast via the compression paddle and/or via the imaging detector "top" surface. The electrical signal representative of a force level may be filtered or converted by one or more circuits or modules described herein into a value that indicates movement. This movement signal, when compared to other measurements over time, may indicate movement of the patient undergoing an imaging procedure.

Imaging system 100 may include a movement detection circuit 112, configured to receive an electronic force signal from force sensor 110 and filter a movement signal from the received force signal. In some embodiments, the received force signal may include a low frequency compression force signal (e.g., 0 (DC) to <5 Hz), which may be tapped and processed in parallel using movement detection circuit 112. Movement detection circuit 112 may include one or more components to process and filter the force signal, including a DC signal block, such as a blocking capacitor to remove the DC and low frequency components of the force signal, leaving a higher frequency (AC) component, referred to herein as a movement signal. One or more analog circuits may filter and apply gain to the higher frequency (AC) signal components to improve signal-to-noise ratio, if needed. The resulting movement signal may include motion artifacts from the original force signal. As described later, one or more modules, such as movement analysis module 114 may include a digital processing unit and corresponding software to analyze the output from movement detection circuit 112.

In an embodiment, a movement analysis module 114 may include one or more analog circuits, such as a tuned differentiator, to detect movement of human tissue compressed within imaging system 100 using a received movement signal from movement detection circuit 112. In some embodiments, movement analysis module 114 may include hardware and/or software modules configured to accept the movement signal from movement detection circuit 112, and detect tissue movement caused by the patient. An exemplary logic flow illustrating movement detection by movement analysis module 114 is set forth within FIG. 4. By way of example and not limitation, movement may be caused by respiratory activity, cardiac activity, or muscular movements (voluntary or involuntary) by the patient. Movement analysis module 114 may be configured with a movement threshold value, beyond which, movement of the patient is detected and communicated to an image correction module 116.

Image correction module 116 may be configured to receive a determination from movement analysis module 114 that movement has been detected. The determination may include data indicating a movement time and movement level in some embodiments, and the determination may be used to determine a corrective action to be taken. Techniques described herein strive to improve image quality, even in situations where movement is detected, reduce patient radiation exposure when possible, and reduce the time required for patients to undergo imaging procedures. Exemplary corrective actions are described herein with respect to FIGS. 5, 7, and 8 however, other corrective action may be taken consistent with these goals, in some embodiments.

A database of movement criteria. 118 may be used by image correction module 116 to determine the proper corrective action based upon various determinations by movement analysis module 114. For example, criteria within movement criteria database 118 may include movement thresholds, time thresholds for delay, image quality criteria, thresholds indicating the maximum number of images that can be deleted from an image sequence due to detected movement, and other criteria necessary to determine and take corrective actions. In an example, image correction module 116 may include hardware and/or software configured consistent with the techniques described herein to take one or more corrective actions when movement exceeding a threshold has been detected. As described further with respect to FIG. 5, certain movement determinations may be handled in different ways. In an embodiment, image improvements may be made by deleting images associated with movement above a threshold. In an embodiment, an image capture procedure may be delayed until detected movement has fallen below a threshold. In an embodiment, an image capture procedure may be extended so that a proper exposure can be taken while also excluding images from an imaging sequence impacted by movement. In an embodiment, an image capture procedure may be canceled, reducing patient radiation exposure.

In some embodiments, artifact-based image detection of patient motion as described in the '180 Patent may be combined with the information from the force sensor 110 and the movement detection circuit 112 in the movement analysis module 114. In one example, the movement analysis module 114 may correlate the information received from the motion detection circuit with the artifact based image detection.

In an embodiment, display device 121 may include a user interface configured to receive and display an image along with information with respect to detected movement and any corrective actions taken in response. In an embodiment, display 124 may be configured to display an alert or movement score (FIGS. 7 and 8) indicating to a practitioner that movement was detected and/or a level of detected movement. Optionally, imaging system 100 may include an indicator 126, which may include an LED, that may be triggered when movement exceeding a threshold has been detected during a procedure. In addition to a notification via the user interface of display 124 or optional indicator 126, other techniques for notification of detected movement may be used. Non-limiting examples include audio notification, haptic notification, other visual indication using lights, and/or one or more prompts within the user interface.

FIG. 2 illustrates an imaging system 200 according to an embodiment. Imaging system 200 illustrates exemplary components most relevant to the techniques described herein and may include other components not depicted within FIG. 2. Upper portion 202 including imaging source 204, which may be an x-ray source in some embodiments and may be consistent with imaging source 106, described above with respect to FIG. 1.

Compression paddle 206 may be mounted to an arm, itself connected to a frame connected to a body of the imaging system 200. Compression paddle 206 may be lowered onto human tissue during an imaging procedure. Certain imaging procedures, such as mammography, may require compression of human tissue between compression paddle 206 and another surface, such as the surface of detector 214, which may be consistent with detector 108, described above with respect to FIG. 1.

Force sensor module 208 may be contained within compression paddle 206, and may detect force 212 imparted on breast 210, which is placed between compression paddle 206 and imaging detector 214. The detected force may represent a measurement of force applied superior to the breast via the compression paddle 206 and/or via the imaging detector 214 "top" surface. Additionally or separately, a force sensor module may be incorporated into the imaging detector 214 component. In this configuration, the force sensor module incorporated into the imaging detector 214 may operate in the same manner as the force sensor module 208 and may measure the DC and AC compression signals applied by the compression paddle 206 upon the human tissue (breast 210) that is placed between the compression paddle 206 and upon the surface of the imaging detector 214. As set forth above, force sensor 208, or the optional force sensor incorporated into the imaging detector 214, may include a strain gauge, piezoelectric sensor, load cell, or other sensor capable of measuring the force applied to human tissue compressed between a compression paddle and an opposite detector plane. In some embodiments, force sensor 208, or the optional force sensor incorporated into the imaging detector 214, may include an analog filter, gain circuits for signal conditioning, and/or an analog-to-digital converter for signal capture. The output of force sensor 208, or the optional force sensor incorporated into the imaging detector 214, may be an electrical signal representative of a force level, which may be filtered or converted by one or more circuits or modules described herein into a value that indicates movement. This movement signal, when compared to other measurements over time, may indicate movement of the patient undergoing an imaging procedure.

In an embodiment, the described force sensor modules may include one or more circuitry components comprising a movement detection circuit, such as movement detection circuit 112. In an embodiment, movement detection circuit 216 may be implemented separate from force sensor 208, and may receive a signal therefrom. As described with respect to FIG. 1, movement detection circuit 216 may receive a force signal from force sensor 208 and filter a high-frequency AC component from the received force signal into a movement signal indicating movement of the human tissue compressed between compression paddle 206 and a surface of detector 214.

Movement analysis module 218, which may be implemented in hardware and/or software, may be configured to determine whether a received movement signal has exceeded a movement threshold. In some embodiments, the movement analysis module 218 may be present separate from force sensor 208, and may be within, the optional force sensor incorporated into the imaging detector 214, compression paddle 206 or within another portion of imaging system 200, as illustrated. If a movement threshold has been exceeded, movement analysis module may communicate that determination to image correction module 220, which may be configured to take corrective action, as described herein with respect to FIGS. 5, 7, and 8.

FIG. 3 illustrates an imaging system 200 according to an embodiment. Elements within FIG. 3 may be similar to like-numbered elements from FIG. 2. The key difference between FIG. 2 and FIG. 3 is the illustration of movement of breast 310. As illustrated, breast 310 may be moved while between compression paddle 306 and a surface of detector 314. This movement may affect a force measurement 312 made by force sensor 308. While a generally up and down movement is illustrated within FIG. 3, it can be appreciated that a variety of movements may be made by breast 310. Movement may be due to a variety of factors, such as relating to cardiac or respiratory movements, sneezing, or voluntarily or involuntarily moving one or more portions of the body that affect the movement of breast 310. As described below, movement of breast 310 may be of any number of types, and may be temporally evaluated by one or more modules of imaging system 300. Evaluation of movement type and movement timing using techniques described herein may provide increased image quality and patient experience while reducing patient exposure to radiation.

Figure 14:
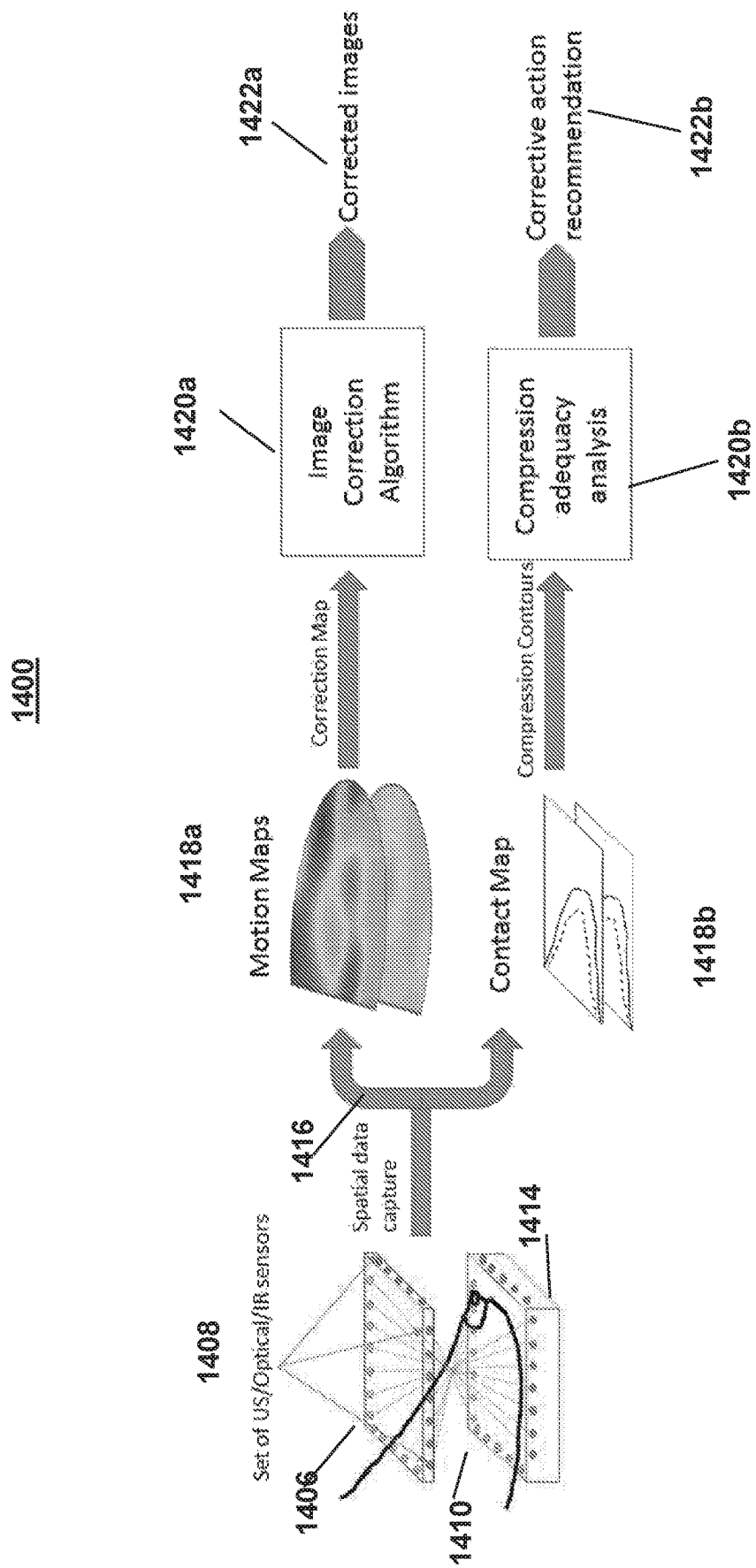
FIG. 14 illustrates an embodiment of an imaging system.

FIG. 14 illustrates another embodiment of an imaging system 1400 where one or more sensors, in combination or alternatively to the force sensor 208, are used. Elements within FIG. 14 may be similar to like-numbered elements from FIG. 1, FIG. 2, and/or FIG. 3. Imaging system 1400 illustrates exemplary components most relevant to the techniques described herein and may include other components not depicted within FIG. 14. The imaging system 1400 includes a compression paddle 1406, and a detector 1414 disposed a distance away from and parallel to the compression paddle. A breast 1410 is compressed between the compression paddle and the detector 1414. One or more sensors 1408 disposed on or within the compression paddle 1406 and the detector 1414.

The one or more sensors 1408 may comprise a sensor module which may detect motion of the breast 1410. In one example, the sensors 1408 may include one or more photo sensors, infra-red sensors and/or ultrasound or ultrasonic sensors. The motion detected by the sensors may be based on reflected sonic signals, or reflected light signals. In some embodiments, the sensors 1408 may be placed in a grid pattern on or within the compression paddle 1406 and the detector 1414. In other examples, the sensors 1408 may be disposed around the periphery of the compression paddle 1406 and the detector 1414.

By disposing multiple sensors in a pattern, a more detailed understanding of motion of the breast may be obtained. As such, it is appreciated that movement of the breast may not be uniform. For example, some areas of the breast may move more than others. Use of multiple sensors would allow the imaging system 1400 to create a motion map which would visually show the location of movement throughout the surface of the breast. By having a more complete understanding of the location of motion of the breast, the imaging system can determine whether such motion would have a negative effect on the image obtained. In addition, having additional sensors would allow the imaging system to obtain other information such as the amount of contact with the breast, as further discussed below, to determine breast positioning information.

The sensors that may be incorporated into the imaging detector 1414 may include an analog filter, gain circuits for signal conditioning, and/or an analog-to-digital converter for signal capture. The output of sensors 1408 may be electrical signals representative of motion of the breast 1410, which may be filtered or converted by one or more circuits or modules described herein into a plurality of spatial information or data 1416. The spatial information can be combined to create a motion map 1418a. The motion map takes spatial information from each of the sensors 1408 to create a relative representation of motion. The motion map 1408a may describe some areas of the breast 1410 that include more motion than others. The motion map 1408a is a visual representation of the spatial information having some colors (e.g. red) represent higher amount of motion and other colors represent moderate (e.g. yellow) or low (e.g. green) amount of motion. The relative representation of motion may be determined based on spatial information comparison to a threshold or a look up table representing various levels of motion.

In addition, the motion map 1408a may be created for each of the tomosynthesis projections or slices created. For example, FIG. 14 shows two tomosynthesis projections. One projection having larger degree of motion and another projection showing smaller degree of motion. It is appreciated that any number of motion maps may be created based on the number of projections.

The spatial information 1416 may also be used to create a contact map 1418b. It is appreciated by inventors that the entirety of the breast 1410 is not in contact with the compression paddle 1406 and the detector 1414. There may be a line, called the "uncompressed tissue line" or the "paddle contact line" in an image, which defines a contour of contact points of breast with paddle/detector. The location of line of compression with respect to breast profile can also be used to give a metric of the adequacy of the compression. For example, the larger the area of uncompressed tissue, the less adequate the compression. It is further appreciated by the inventors that less than adequate level of compression results in poor image quality. The contact map 1418b shows the level of contact with the breast 1410. The contact map 1418b can be used to determine or define a roll off region, which is the region where the breast is uncompressed. The location of the paddle contact line and the size of the roll off region could also can be useful in special image processing techniques in uncompressed vs compressed breast areas. The location of line of compression with respect to breast profile can also be used to give an idea of how adequate the compression is, which can be used in determining the adequacy of positioning of the breast.

The information from the motion map can be input into an image correction module 1420a. The image correction module 1420a is similar to the image correction modules 116 and 220 described above with respect to FIGS. 1, 2, and 3, and may perform the functions and correction as further described with reference to FIGS. 4 and 5.

Similarly, the information from the contact map 1418b may be input in a compression adequacy analysis module 1420b. The image correction module 1420b may be similar to the image correction modules 116 and 220, with the deference of that a threshold of compression is used, rather than a motion threshold is used, to compare the current compression contours to the threshold of compression contours. The image correction module 1420b may perform the functions and corrections as further described with reference to FIGS. 4 and 5. For example, if currently compression contours are below a threshold of compression contours, image capture may be delays until contours are above the threshold, or image capture may be cancelled if the delay exceeds a threshold. In at leak one example, one or more alerts or alarms as discussed above may be generated to notify the technologist that compression is inadequate and the patient may need to be repositioned.

Included herein is a set of flow charts representative of exemplary methodologies for performing novel aspects of the disclosed architecture. While, for purposes of simplicity of explanation, the one or more methodologies shown herein, for example, in the form of a flow chart or flow diagram, are shown and described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology could alternatively be represented as a series of interrelated states or events, such as in a state diagram. Moreover, not all acts illustrated in a methodology may be required for a novel implementation.

Figure 4:
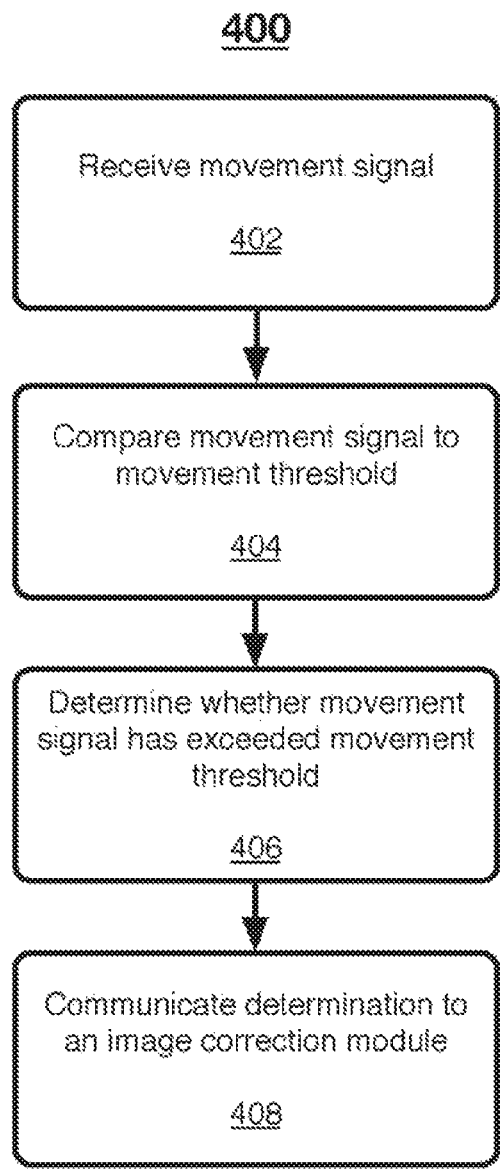
FIG. 4 illustrates a logic flow according to an embodiment.

FIG. 4 illustrates a logic flow 400 according to an embodiment. The logic flow 400 may be representative of some or all of the operations executed by one or more embodiments described herein, such as imaging system 100, for example. Specifically, logic flow 400 may illustrate operations performed by a movement analysis module, such as movement analysis module 114.

At 402, a movement analysis module may receive a movement signal from a force sensor and/or movement detection circuit. The movement signal may include motion artifacts indicating that human tissue, currently under compression during an imaging procedure, has moved. Using hardware and/or software components, the received movement signal may be evaluated to isolate data indicating movement and a value may be assigned indicating a movement level. In an embodiment, a baseline movement signal may be first evaluated, indicating a baseline movement value, or a baseline movement value may be stored within an imaging system. Subsequent movement signals may be received and compared to the baseline movement value to identify motion artifacts within the subsequent movement signals.

At 404, the movement analysis module may compare subsequently received movement signals, and any motion artifacts identified therein, to a movement threshold, which may be predetermined and stored within a non-transitory computer-readable storage medium. In some embodiments, thresholds may be dynamically determined by an imaging system during the image capture process based, at least in part, on a detected image quality assessment taken in near real-time. In other embodiments, a movement threshold may be pre-determined and stored within an imaging system.

At 406, the movement analysis module may determine whether the received movement signal has exceeded the movement threshold and, at 408, the movement analysis module may communicate the determination to an image correction module, which is discussed in more detail below. The determination, in some embodiments, may include an indication that movement has been detected, a movement value, a timestamp, a frame identifier, or other information that may be necessary for an image correction module to take appropriate corrective measures based upon the detected movement.

Figure 5:
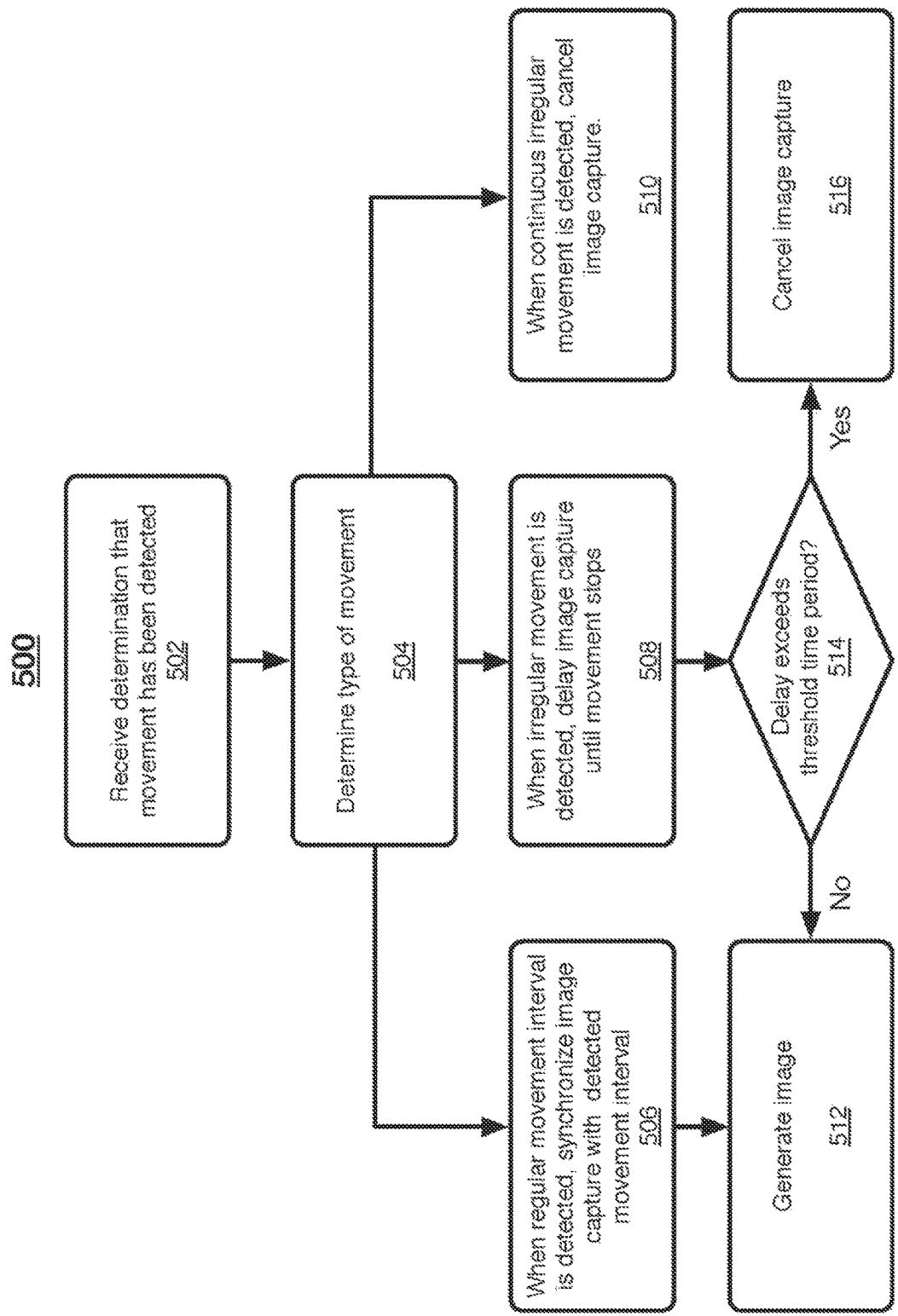
FIG. 5 illustrates a logic flow according to an embodiment.

FIG. 5 illustrates a logic flow 500 according to an embodiment. The logic flow 500 may be representative of some or all of the operations executed by one or more embodiments described herein, such as imaging system 100, for example. Specifically, logic flow 500 may illustrate operations performed by an image correction module, such as image correction module 116.

At 502, an image correction module may receive a determination that movement has been detected. In some embodiments, any movement may be communicated to the image correction module. In other embodiments, only movement that exceeds a threshold, as described herein, may be communicated to the image correction module. The determination, in some embodiments, may include an indication that movement has been detected, a movement value, a timestamp, a frame identifier, or other information that may be necessary for an image correction module to take appropriate corrective measures based upon the detected movement.

At 504, the image correction module may determine a type of movement based upon one or more received movement determinations. For example, a movement may be categorized as a regular movement when it is repetitive and generally within a regular time interval. This type of movement may indicate a patient is breathing, or moving in a regular fashion. In another example, movement may be categorized as irregular. A single irregular movement may indicate a patient has shifted positions, or sneezed, for example. In yet another example, movement may be categorized as continuously irregular. A determination of movement type may be based, in part, on a movement value and/or timestamp, for example. In at least one example, a determination of the movement may be that the movement is localized to one or more tomosynthesis slices.

At 506, when a regular movement that is repetitive and generally within a regular time interval is detected, the image correction module may configure the image capture to be synchronized with the regular movement. In this manner, image capture may be performed during a time period in which movement is not detected, and skipped during a time period in which movement is detected. The synchronized image sequence may be generated at 512, and may include only images in which movement has not been detected, or detected movement is below a threshold amount.

At 508, when irregular movement is detected, the image correction module may delay image capture for a period of time, allowing the movement to stop so an image is not negatively impacted. As described herein, some embodiments may flag image captured images taken during a movement, and those images may be removed from an imaging sequence used to generate an image.

At 510, if a termination of movement is localized to one or more tomosynthesis slices. The slices may be removed or cancelled from the tomosynthesis stack that are associated with movement above a threshold.

At 514, if irregular movements continue during the delay period, the delay may be extended until movement stops. However, since in some cases the patient may be exposed to x-ray radiation during the delay, a time period threshold may be set for which the image capture may be canceled if the delay lasts beyond the threshold. Thus, an image may be generated at 512 if the delay is within the time threshold, and the image capture may be canceled at 516 if the delay period extends beyond the time threshold. In this manner, an imaging system may be able to compensate for some movement, and generate higher quality images by delaying capture until movement is no longer detected, while at the same time canceling an image and limiting patient radiation exposure when a satisfactory image cannot be obtained due to excessive irregular movement.

During image generation at 512, certain embodiments may correlate images with detected movement and flag images in which movement was detected. In this manner, images flagged with movement may be removed from a resulting imaging sequence, thus, improving overall image quality despite detecting motion within the imaging procedure. In some cases, many images may be flagged as occurring during movement and the entire imaging sequence may need to be canceled. Based upon a particular procedure, for example, a threshold may be set such that an image correction module may determine whether the process of deleting images may result in a usable image sequence, or if the imaging sequence needs to be canceled due to excessive movement during the imaging procedure.

Figure 6:
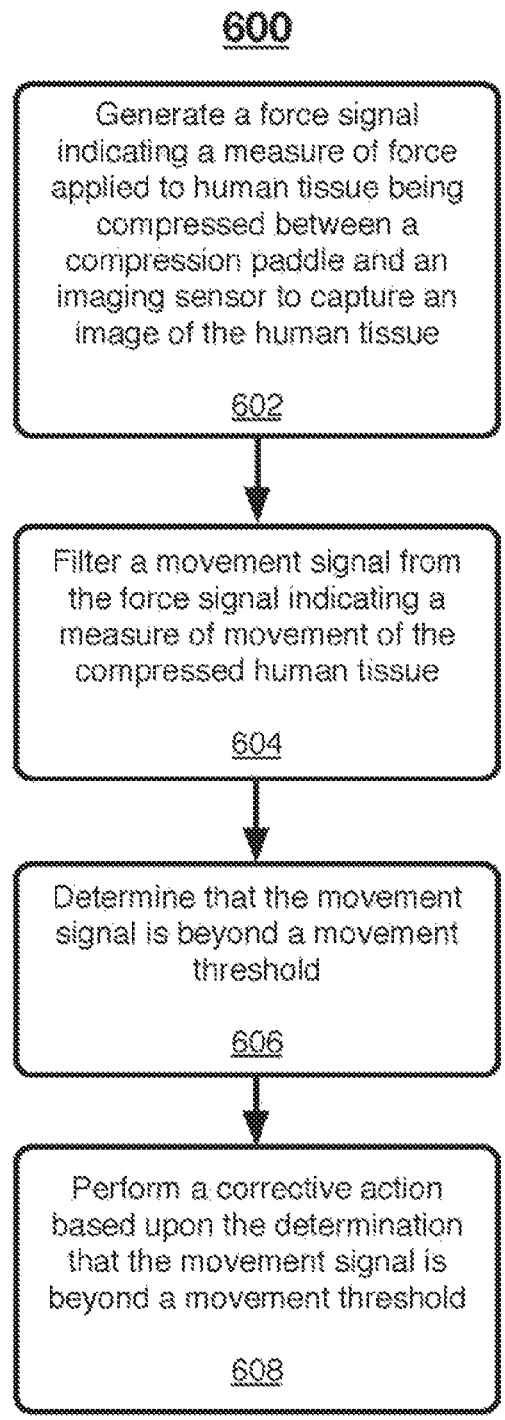
FIG. 6 illustrates a logic flow according to an embodiment.

FIG. 6 illustrates a logic flow 600 according to an embodiment. The logic flow 600 may be representative of some or all of the operations executed by one or more embodiments described herein, such as imaging systems 100, 200, and/or 300, for example. At 602, a force sensor may generate a force signal indicating a measure of force applied to human tissue being compressed between a compression paddle and an imaging detector to capture an image of the human tissue. As set forth above, a force sensor may include a strain gauge, piezoelectric sensor, load cell, or other sensor capable of measuring the force applied to human tissue compressed between a compression paddle and an opposite detector plane. In some embodiments, a force sensor may include an analog filter, gain circuits for signal conditioning, and/or an analog-to-digital converter for signal capture. The output of a force sensor may be an electrical signal representative of a force level, which may be filtered or converted by one or more circuits or modules described herein into a value that indicates movement. This movement signal, when compared to other measurements over time, may indicate movement of the patient undergoing an imaging procedure.

At 604, a movement detection circuit may filter the received force signal and isolate a movement signal from therein. The movement signal may indicate a level of force, and in some cases may indicate that a patient has moved during image capture in a manner that is detrimental to the quality of a resulting image. As set forth above, the movement detection circuit may be configured to receive an electronic force signal from a force sensor and filter a movement signal from the received force signal. In some embodiments, the received force signal may include a low frequency compression force signal (e.g., 0 (DC) to <5 Hz), which may be tapped and processed in parallel using the movement detection circuit. Further, the movement detection circuit may include one or more components to process the force signal, including a DC signal block, such as a blocking capacitor to remove the DC and low frequency components of the force signal, leaving a higher frequency (AC) component, referred to herein as a movement signal. One or more analog circuits may filter and apply gain to the higher frequency (AC) signal components to improve signal-to-noise ratio, if needed. The resulting movement signal may include motion artifacts from the original force signal.

At 606, a movement analysis module may determine whether a detected movement is beyond a movement threshold. The movement analysis module may include one or more analog circuits, such as a tuned differentiator, to detect movement of human tissue compressed within an imaging system using a received movement signal from the movement detection circuit. In some embodiments, the movement analysis module may include hardware and/or software modules configured to accept the movement signal from the movement detection circuit, and detect tissue movement caused by the patient. An exemplary logic flow illustrating movement detection by a movement analysis module is set forth within FIG. 4. By way of example and not limitation, movement may be caused by respiratory activity, cardiac activity, or muscular movements (voluntary or involuntary) by the patient. A movement analysis module may be configured with a movement threshold value, beyond which, movement of the patient is detected and communicated to an image correction module at 608.

At 608, when movement is beyond a threshold, an image correction module may perform a corrective action, which may include one or more of a variety of actions that improve image quality and reduce patient exposure to radiation. An image correction module may be configured to receive a determination from movement analysis module that movement has been detected. The determination may include data indicating a movement time and movement level in some embodiments, and the determination may be used to determine a corrective action to be taken, some of which are described with respect to FIG. 5, and below with respect to FIGS. 7 and 8. Techniques described herein strive to improve image quality, even in situations where movement is detected, reduce patient radiation exposure when possible, and reduce the time required for patients to undergo imaging procedures. While exemplary corrective actions are described herein, other corrective action may be taken consistent with these goals, in some embodiments.

Figure 7:
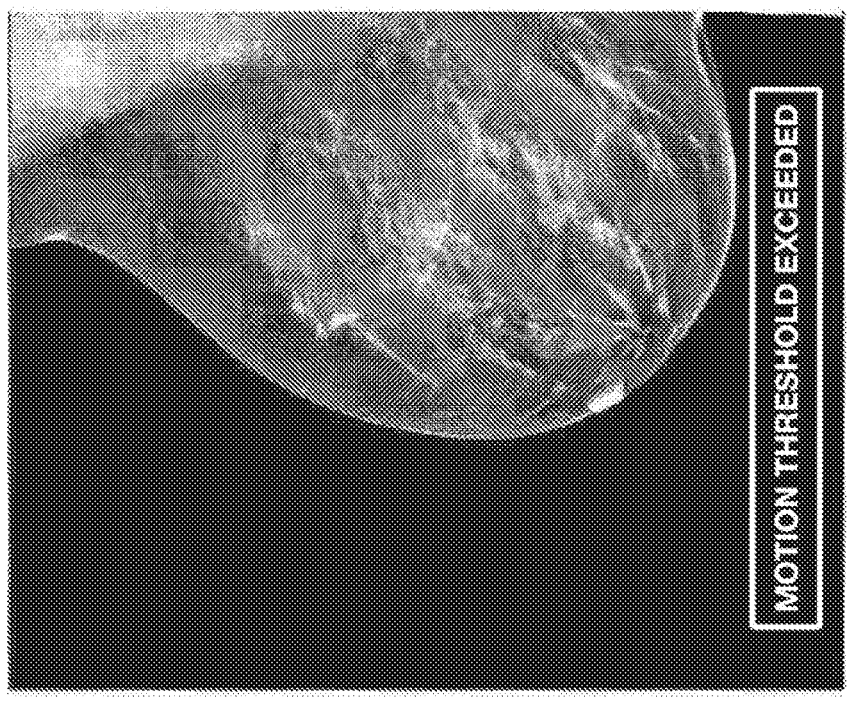
FIG. 7 illustrates a generated image according to an embodiment.

FIG. 7 illustrated a generated image 700 according to an embodiment. Generated image 700 may be generated by one or more imaging systems described herein, for example, imaging systems 100, 200, and/or 300. In some embodiments, corrective actions may include visual indications within a graphical user interface of a display during or after an imaging procedure, using an indicator of an imaging system, and/or using a graphical indication on a generated image itself. FIG. 7 illustrates an alert 702, which may be displayed on a display of an imaging system, indicating to a practitioner or patient that movement was detected during the imaging procedure. Such an indication may alert those viewing the image that quality issues may be fixed by reducing motion in subsequent imaging procedures.

Figure 8:
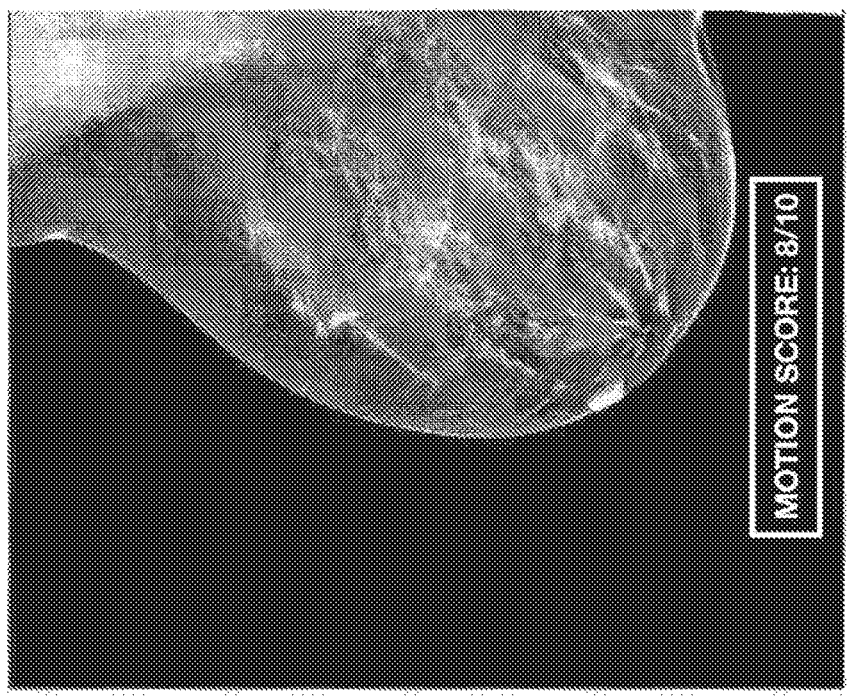
FIG. 8A illustrates a generated image according to an embodiment.
FIG. 8B illustrates a system of facilities according to an embodiment.
FIG. 8C illustrates a logic flow according to an embodiment.

FIG. 8 illustrates a generated image 800 according to an embodiment. Generated image 700 may be generated by one or more imaging systems described herein, for example, imaging systems 100, 200, and/or 300. In some embodiments, corrective actions may include visual indications within a graphical user interface of a display during or after an imaging procedure, using an indicator of an imaging system, and/or using a graphical indication on a generated image itself. FIG. 8 illustrates an alert 802 indicating a motion score, which may indicate a score on a relative scale of motion detected during an imaging procedure. In an example, a minimum and maximum level of movement may be stored within a non-transitory computer-readable storage medium of an imagine system. Once movement has been detected, an image correction module may perform a calculation of the detected movement and determine a score based upon the stored minimum and maximum values. In this manner, a practitioner or patient may be provided with an indication of how much movement was detected, and may take steps to improve image quality in subsequent imaging procedures. In another example, the score may be pass/fail score, with pass meaning that the motion is below the threshold and no corrective action is needed, and fail meaning that corrective action is needed. Other scoring methodologies are contemplated. In one embodiment, the positioning information from many images can be aggregated into analytics and supplied to the facility and other entities for the purposes of training, education, analytics and compliance.

Figure 8B:
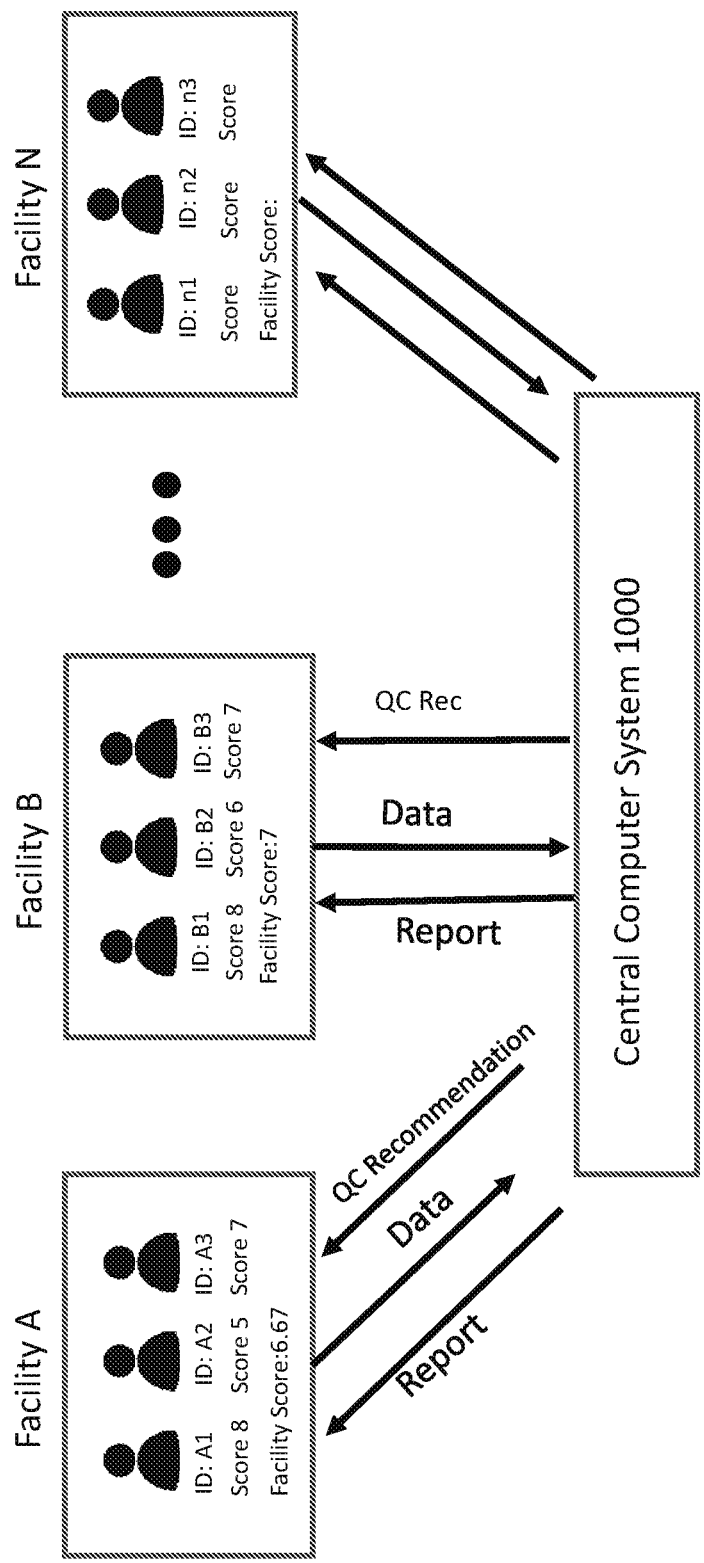

FIG. 8B shows the positioning information collected and analyzed according to one embodiment. Each image may be associated with a radiology technologist or technologist who took the image (e.g. a technologist identification number) and associated with a patient positioning score for that image as described above. The information may be stored in the imaging system 100. The information may then be transmitted to a centralized system, such as the system 1000 described below with reference to FIG. 10. The scores, the technologist IDs, and other information collected from the imaging system 100 may be aggregated over time. The scores for a particular technologist can be analyzed, for example, by the centralized system 100, to determine if one or more corrective actions are needed. In one example, a particular technologist's average score can be compared to average scores of others or other technologists in that particular facility, or in other facilities. If the centralized system determined that the technologist's scores are below a particular threshold, the technologist may be recommended for patient positioning education or quality control improvements. In one example, a look-up table or algorithm determines whether corrective action is needed and what type of action to recommend based in part on the score.

Additional examples of use of the positioning information may include compliance with Federal Regulations, such as the Mammography Quality Standards Act (MQSA) and the Enhancing Quality Using the Inspection Program or EQUIP initiative. The MQSA requires that the images taken at a facility must comply with certain quality standards. Poor positioning is a factor in most deficiencies and failures of clinical images to meet quality standards. EQUIP requires regular review of images, corrective procedures when clinical images are of poor quality, including a mechanism for providing ongoing feedback to technologists or other designated personnel, and oversight of quality control records. The analytics described above can be used to generate reports of compliance with federal regulations. For example, the report may be automatically generated on a periodic basis that includes information such as the score information for that facility, the number of times corrective procedures were taken, the number of times that corrective measures such as education and quality control measures were recommended and were taken. Such reports can be stored and provided if needed to federal regulators to ensure compliance.

Figure 8C:
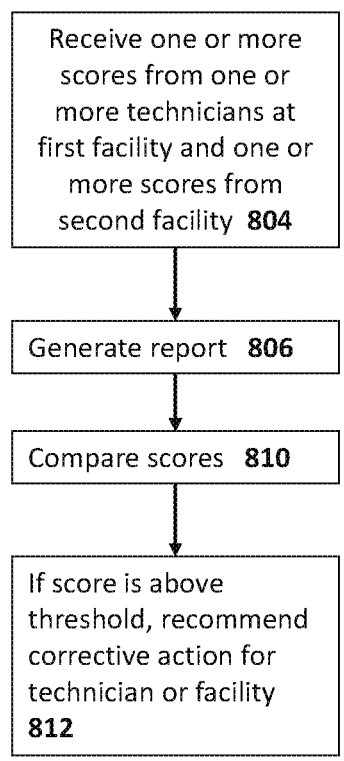

FIG. 8C illustrates a logic flow 814 according to an embodiment. The logic flow 814 may be representative of some or all of the operations executed by one or more embodiments described herein, such as systems 100, 200, and/or 300, 1000, for example. In step 804 information, including one or more scores, is received from one or more technologists at a first facility. Positioning information, including one or more scores, is received from one or more technologists at a second facility. In step 806, the information may be analyzed and a report is generated. The report may be provided to the facility for which is it associated. In step 810, the information may be compared. In one example, the scores may be compared within the facility, for instance, to score the technologists relative to each other. In another example, the scores may be compared to scores at other facilities. In step 812, the scores may be compared to a threshold to determine if the particular technologist is above or below the threshold. If above, the technologist is adequately performing positioning patient positioning. If below the threshold, the technologist may require corrective action, for example, education or QC corrective actions. In addition, the scores for all the technologists in a particular facility may be compared to a threshold. If the scores for the facility are above the threshold, a report is generated of compliance to federal regulations. If the scores for the facility are below the threshold, QC for the facility are recommended. A report is generated with non-compliance and recommendations for QC.

Figure 9:
FIG. 9 illustrates an article of manufacture according to an embodiment.

FIG. 9 illustrates an article of manufacture according to an embodiment. Storage medium 900 may comprise any computer-readable storage medium or machine-readable storage medium, such as an optical, magnetic or semiconductor storage medium. In some embodiments, storage medium 900 may comprise a non-transitory storage medium. In various embodiments, storage medium 900 may comprise an article of manufacture. In some embodiments, storage medium 900 may store computer-executable instructions, such as computer-executable instructions to implement logic flow 900, for example. Examples of a computer-readable storage medium or machine-readable storage medium may include any tangible media capable of storing electronic data, including volatile memory or non-volatile memory, removable or non-removable memory, erasable or non-erasable memory, writeable or re-writeable memory, and so forth. Examples of computer-executable instructions may include any suitable type of code, such as source code, compiled code, interpreted code, executable code, static code, dynamic code, object-oriented code, visual code, and the like. The embodiments are not limited to these examples.

Figure 10:
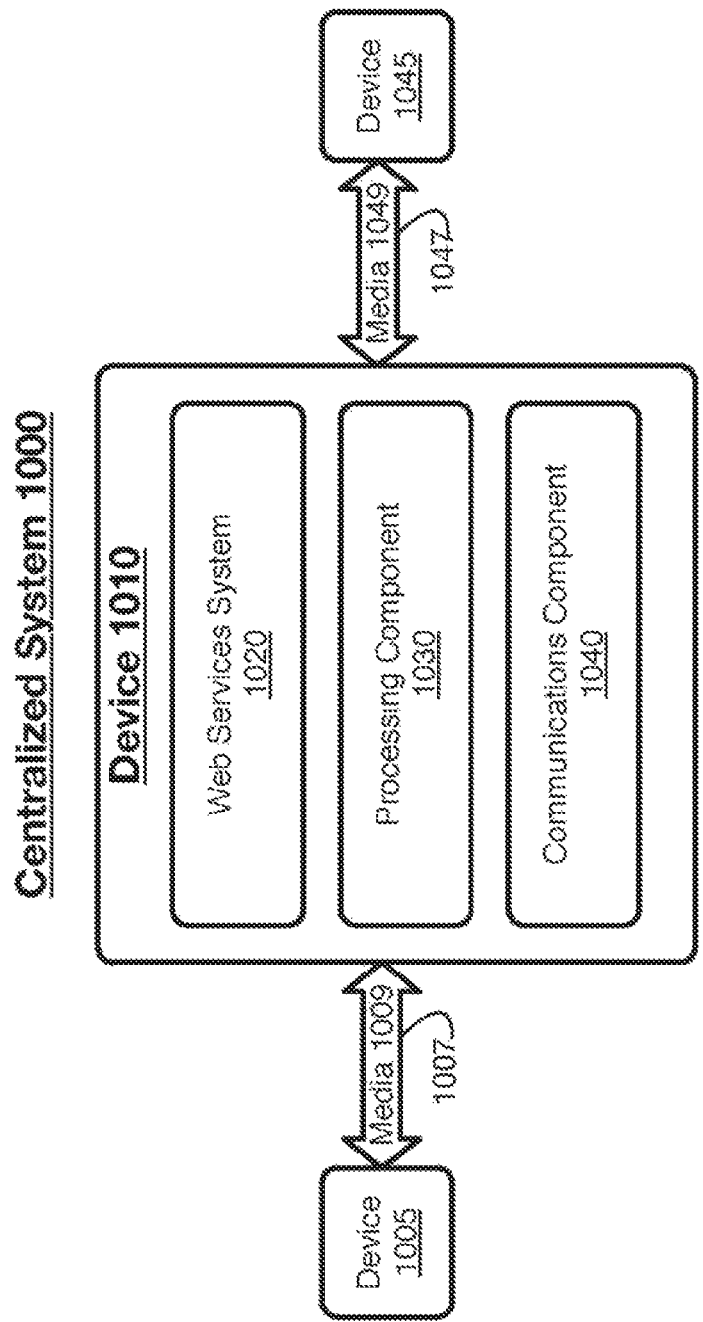
FIG. 10 illustrates an embodiment of a centralized system.

FIG. 10 illustrates a block diagram of a centralized system 1000. The centralized system 1000 may implement some or all of the structure and/or operations for the web services system 1020 in a single computing entity, such as entirely within a single device 1010.

The device 1010 may comprise any electronic device capable of receiving, processing, and sending information for the web services system 1020. Examples of an electronic device may include without limitation an imaging system, client device, a mobile computing device, a computer, a server, a distributed computing system, multiprocessor systems, or combination thereof. The embodiments are not limited in this context.

The device 1010 may execute processing operations or logic for the web services system 1020 using a processing component 1030. The processing component 1030 may comprise various hardware elements, software elements, or a combination of both. Examples of hardware elements may include devices, logic devices, microprocessors, circuits, circuit elements (e.g., transistors, resistors, capacitors, inductors, and so forth), integrated circuits, and so forth. Examples of software elements may include software programs, machine programs, operating system software, middleware, firmware, functions, methods, procedures, software interfaces, application program interfaces (API), words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints, as desired for a given implementation.

The device 1010 may execute communications operations or logic for the web services system 1020 using communications component 1040. The communications component 1040 may implement any well-known communications techniques and protocols, such as techniques suitable for use with packet-switched networks (e.g., public networks such as the Internet, private networks such as an enterprise intranet, and so forth), circuit-switched networks (e.g., the public switched telephone network), or a combination of packet-switched networks and circuit-switched networks (with suitable gateways and translators). The communications component 1040 may include various types of standard communication elements, such as one or more communications interfaces, network interfaces, wireless transmitters/receivers (transceivers), wired and/or wireless communication media, physical connectors, and so forth. By way of example, and not limitation, communication media 1009, 1049 include wired communications media and wireless communications media.

The device 1010 may communicate with other devices 1005, 1045 over a communications media 1009, 1049, respectively, using communications signals 1007, 1047, respectively, via the communications component 1040. The devices 1005, 1045, may be internal or external to the device 1010 as desired for a given implementation.

For example, device 1005 may correspond to a client device such as a phone used by a user. Signals 1007 sent over media 1009 may therefore comprise communication between the phone and the web services system 1020 in which the phone transmits a request and receives a web page or other data in response.

Figure 11:
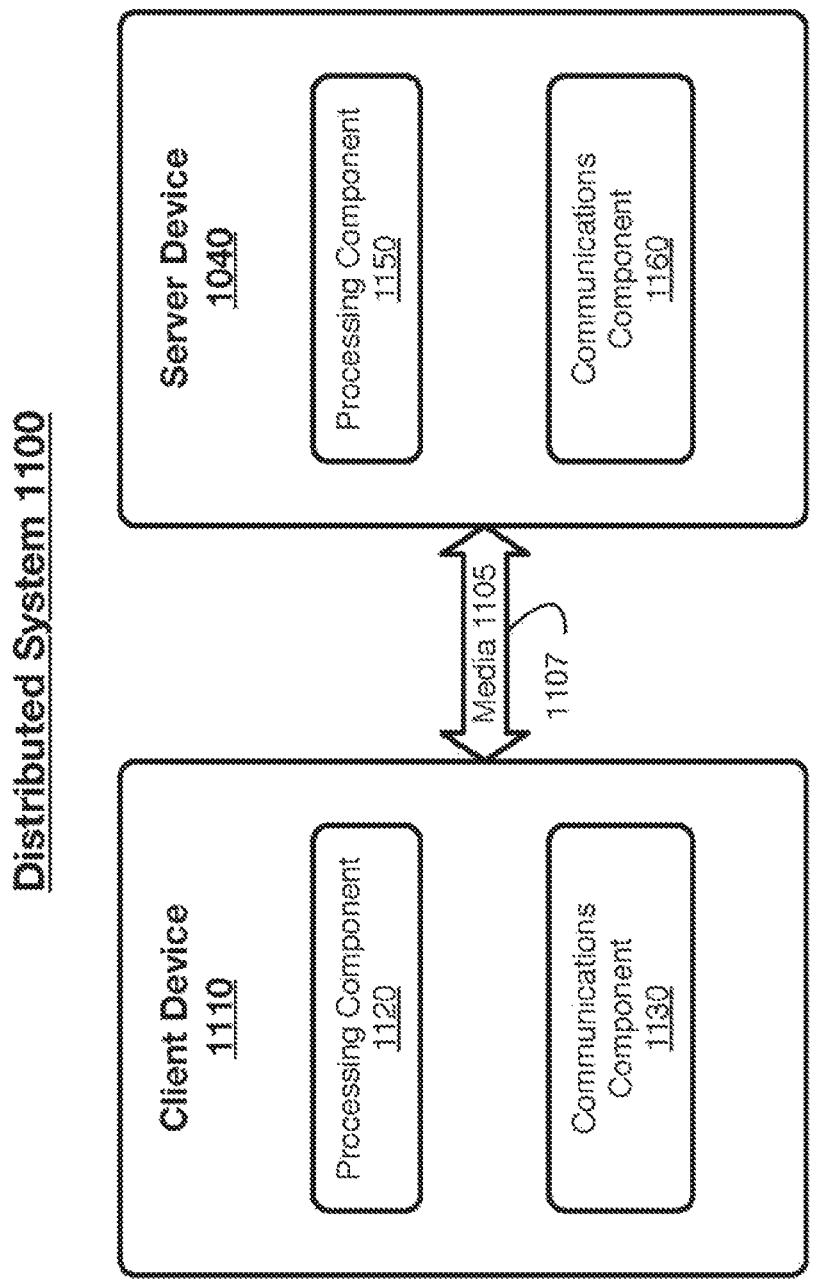
FIG. 11 illustrates an embodiment of a distributed system.

FIG. 11 illustrates a block diagram of a distributed system 1100. The distributed system 1100 may distribute portions of the structure and/or operations for the disclosed embodiments across multiple computing entities. Examples of distributed system 1100 may include without limitation a client-server architecture, a peer-to-peer architecture, a shared database architecture, and other types of distributed systems. The embodiments are not limited in this context.

The distributed system 1100 may comprise a client device 1110 and a server device 1140. In general, the client device 1110 and the server device 1140 may be the same or similar to the client device 1010 as described with reference to FIG. 10. For instance, the client system 1110 and the server system 1140 may each comprise a processing component 1120, 1150 and a communications component 1130, 1160 which are the same or similar to the processing component 1030 and the communications component 1040, respectively, as described with reference to FIG. 10. In another example, the devices 1110, 1140 may communicate over a communications media 1105 using communications signals 1107 via the communications components 1130, 1160.

The client device 1110 may comprise or employ one or more client programs that operate to perform various methodologies in accordance with the described embodiments. In one embodiment, for example, the client device 1110 may implement some steps described with respect to FIGS. 4-6.

The server device 1140 may comprise or employ one or more server programs that operate to perform various methodologies in accordance with the described embodiments. In one embodiment, for example, the server device 1140 may implement some steps described with respect to FIGS. 4-6.

Figure 12:
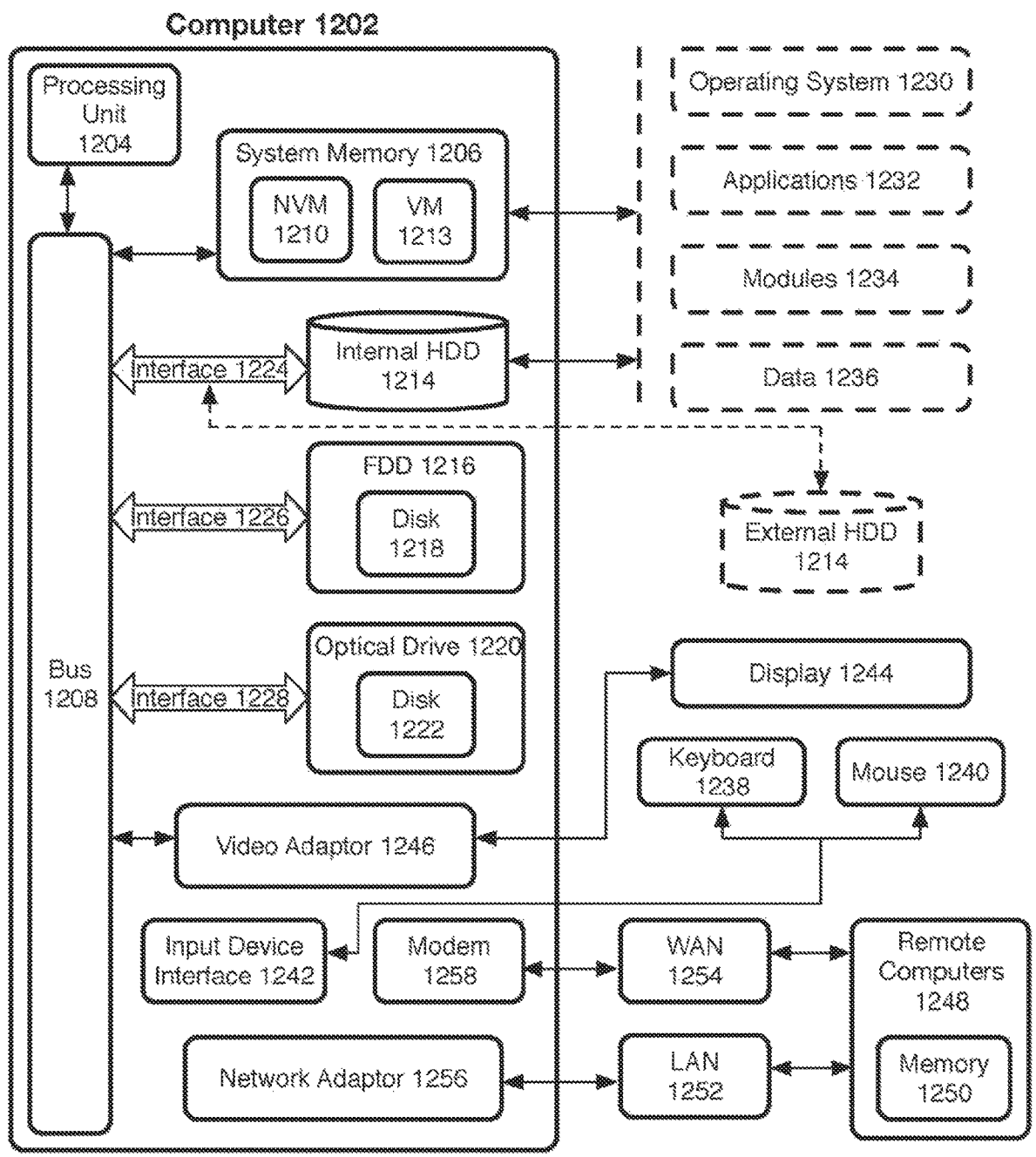
FIG. 12 illustrates an embodiment of a computing architecture.

FIG. 12 illustrates an embodiment of an exemplary computing architecture 1200 suitable for implementing various embodiments as previously described. In one embodiment, the computing architecture 1200 may comprise or be implemented as part of an electronic device. Examples of an electronic device may include those described herein. The embodiments are not limited in this context.

As used in this application, the terms "system" and "component" are intended to refer to a computer-related entity, either hardware, a combination of hardware and software, software, or software in execution, examples of which are provided by the exemplary computing architecture 1200. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 1200 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 1500.

As shown in FIG. 12, the computing architecture 1200 comprises a processing unit 1204, a system memory 1206 and a system bus 1208. Dual microprocessors, multi-core processors, and other multi-processor architectures may also be employed as the processing unit 1204.

The system bus 1208 provides an interface for system components including, but not limited to, the system memory 1206 to the processing unit 1204. The system bus 1208 can be any of several types of bus structure that may further interconnect to a memory bus (with or without a memory controller), a peripheral bus, and a local bus using any of a variety of commercially available bus architectures. Interface adapters may connect to the system bus 1208 via a slot architecture, for example.

The computing architecture 1200 may comprise or implement various articles of manufacture. An article of manufacture may comprise a computer-readable storage medium to store logic, as described above with respect to FIG. 9.

The system memory 1206 may include various types of computer-readable storage media in the form of one or more higher speed memory units, such as read-only memory (ROM), random-access memory (RAM), dynamic RAM (DRAM), solid state memory devices (e.g., USB memory, solid state drives (SSD) and any other type of storage media suitable for storing information.). In the illustrated embodiment shown in FIG. 12, the system memory 1206 can include non-volatile memory 1210 and/or volatile memory 1213. A basic input/output system (BIOS) can be stored in the non-volatile memory 1210.

The computer 1202 may include various types of computer-readable storage media in the form of one or more lower speed memory units, including an internal (or external) hard disk drive (HDD) 1214, a magnetic floppy disk drive (FDD) 1216 to read from or write to a removable magnetic disk 1218, and an optical disk drive 1220 to read from or write to a removable optical disk 1222 (e.g., a CD-ROM, DVD, or Blu-ray), The HDD 1214, FDD 1216 and optical disk drive 1220 can be connected to the system bus 1208 by a HDD interface 1224, an FDD interface 1226 and an optical drive interface 1228, respectively. The HDD interface 1224 for external drive implementations can include at least one or both of Universal Serial Bus (USB) and IEEE 1394 interface technologies.

The drives and associated computer-readable media provide volatile and/or nonvolatile storage of data, data structures, computer-executable instructions, and so forth. For example, a number of program modules can be stored in the drives and memory units 1210, 1213, including an operating system 1230, one or more application programs 1232, other program modules 1234, and program data 1236. In one embodiment, the one or more application programs 1232, other program modules 1234, and program data 1236 can include, for example, the various applications and/or components to implement the disclosed embodiments.

A user can enter commands and information into the computer 1202 through one or more wire/wireless input devices, for example, a keyboard 1238 and a pointing device, such as a mouse 1240. Other input devices may include microphones, infra-red (IR) remote controls, radio-frequency (RF) remote controls, game pads, stylus pens, card readers, dangles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 1204 through an input device interface 1242 that is coupled to the system bus 1208, but can be connected by other interfaces such as a parallel port, IEEE 1394 serial port, a game port, a USB port, an IR interface, and so forth.

A display 1244 is also connected to the system bus 1208 via an interface, such as a video adaptor 1246. The display 1244 may be internal or external to the computer 1202. In addition to the display 1244, a computer typically includes other peripheral output devices, such as speakers, printers, and so forth.

The computer 1202 may operate in a networked environment using logical connections via wire and/or wireless communications to one or more remote computers, such as a remote computer 1248. The remote computer 1248 can be a workstation, a server computer, a router, a personal computer, portable computer, microprocessor-based entertainment appliance, a peer device or other common network node, and typically includes many or all of the elements described relative to the computer 1202, although, for purposes of brevity, only a memory/storage device 1250 is illustrated. The logical connections depicted include wire/wireless connectivity to a local area network (LAN) 1252 and/or larger networks, for example, a wide area network (WAN) 1254. Such LAN and WAN networking environments are commonplace in offices and companies, and facilitate enterprise-wide computer networks, such as intranets, all of which may connect to a global communications network, for example, the Internet.

When used in a LAN networking environment, the computer 1202 is connected to the LAN 1252 through a wire and/or wireless communication network interface or adaptor 1256. The adaptor 1256 can facilitate wire and/or wireless communications to the LAN 1252, which may also include a wireless access point disposed thereon for communicating with the wireless functionality of the adaptor 1256.

When used in a WAN networking environment, the computer 1202 can include a modem 1258, or is connected to a communications server on the WAN 1254, or has other means for establishing communications over the WAN 1254, such as by way of the Internet. The modem 1258, which can be internal or external and a wire and/or wireless device, connects to the system bus 1208 via the input device interface 1242. In a networked environment, program modules depicted relative to the computer 1202, or portions thereof, can be stored in the remote memory/storage device 1250. It will be appreciated that the network connections shown are exemplary and other means of establishing a communications link between the computers can be used.

The computer 1202 is operable to communicate with wire and wireless devices or entities using the IEEE 802 family of standards, such as wireless devices operatively disposed in wireless communication (e.g., IEEE 802.11 over-the-air modulation techniques). This includes at least Wi-Fi (or Wireless Fidelity), WiMax, and Bluetooth™ wireless technologies, among others.

Figure 13:
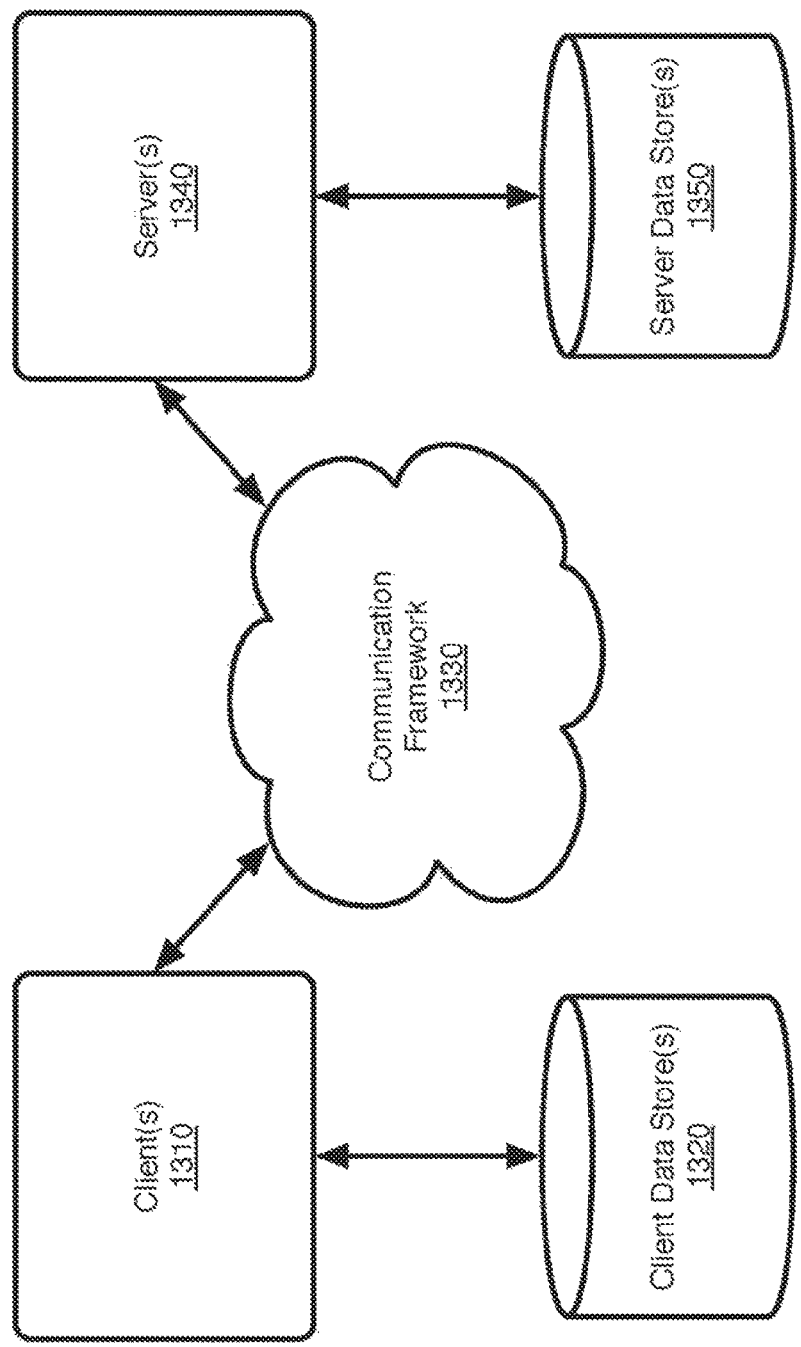
FIG. 13 illustrates an embodiment of a communications architecture.

FIG. 13 illustrates a block diagram of an exemplary communications architecture 1300 suitable for implementing various embodiments as previously described. The communications architecture 1300 includes various common communications elements, such as a transmitter, receiver, transceiver, radio, network interface, baseband processor, antenna, amplifiers, filters, power supplies, and so forth. The embodiments, however, are not limited to implementation by the communications architecture 1300.

As shown in FIG. 13, the communications architecture 1300 comprises includes one or more clients 1310 and servers 1340. The clients 1310 may implement the client device 1110, for example. The servers 1340 may implement the server device 1140, for example. The clients 1310 and the servers 1340 are operatively connected to one or more respective client data stores 1320 and server data stores 1350 that can be employed to store information local to the respective clients 1310 and servers 1340, such as cookies and/or associated contextual information.

The clients 1310 and the servers 1340 may communicate information between each other using a communication framework 1330. The communications framework 1330 may implement any well-known communications techniques and protocols. The communications framework 1330 may be implemented as a packet-switched network (e.g., public networks such as the Internet, private networks such as an enterprise intranet, and so forth), a circuit-switched network (e.g., the public switched telephone network), or a combination of a packet-switched network and a circuit-switched network (with suitable gateways and translators).

The communications framework 1330 may implement various network interfaces arranged to accept, communicate, and connect to a communications network. A network interface may be regarded as a specialized form of an input output interface. Network interfaces may employ connection protocols including without limitation direct connect, Ethernet, wireless network interfaces, cellular network interfaces, and the like.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Further, some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein which form part of one or more embodiments. Rather, the operations are machine operations. Useful machines for performing operations of various embodiments include general purpose digital computers or similar devices.

Various embodiments also relate to apparatus or systems for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove convenient to construct more specialized apparatus to perform the required method steps. The required structure for a variety of these machines will appear from the description given.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible.

The invention claimed is:

1. An imaging system, comprising:
   an imaging detector to capture a plurality of images of human tissue;
   a compression paddle situated apart from the imaging detector to compress the human tissue between the compression paddle and the imaging detector;
   a force sensor to generate a force signal indicating a measure of force applied superior to the human tissue;
   a processor operatively coupled to the imaging detector and the force sensor; and
   a memory coupled to the processor, the memory storing instructions that, when executed by the processor, perform a set of operations comprising:
   filtering a movement signal from force signal indicating a measure of movement of the compressed human tissue;
   determining that the movement signal in a first image of the plurality of images is beyond a movement threshold;
   determining whether deleting the first image from the plurality of images, based upon the determination that the movement signal in the first image is beyond the movement threshold, exceeds an image removal threshold; and
   performing a corrective action based upon the determination that the movement signal is beyond the movement threshold and the determination whether deleting the first image from the plurality of images exceeds the image removal threshold.

2. The imaging system according to claim 1, the force sensor is included within the compression paddle.

3. The imaging system according to claim 1, the corrective action includes determining and displaying the movement score on the display device.

4. The imaging system according to claim 1, the corrective action includes displaying an alert on a display device indicating that the movement threshold has been exceeded.

5. The imaging system according to claim 1, the corrective action includes triggering a visual indicator of the imaging system.

6. The imaging system according to claim 1, wherein determining whether deleting the first image from the plurality of images exceeds the image removal threshold further comprises identifying each image of the plurality of images associated with a movement signal exceeding the movement threshold.

7. The imaging system according to claim 6, wherein determining whether deleting the first image from the plurality of images exceeds the image removal threshold comprises determining that deleting the first image would not exceed the image removal threshold; and
the corrective action comprises deleting the first image from the plurality of images.

8. The imaging system according to claim 7, wherein determining whether deleting the first image from the plurality of images exceeds the image removal threshold comprises determining that deleting the first image would exceed the image removal threshold; and
the corrective action comprises cancelling the imaging sequence.

9. A computer implemented method, comprising:
receiving, from a force sensor, a force signal indicating a measure of force applied superior to human tissue being compressed between a compression paddle and an imaging detector to capture a plurality of images of the human tissue;
filtering a movement signal from the force signal indicating a measure of movement of the compressed human tissue;
determining that the movement signal in a first image of the plurality of images is beyond a movement threshold;
determining whether deleting the first image from the plurality of images, based upon the determination that the movement signal in the first image is beyond the movement threshold, exceeds an image removal threshold; and
performing a corrective action based upon the determination that the movement signal is beyond the movement threshold and the determination whether deleting the first image from the plurality of images exceeds the image removal threshold.

10. The computer-implemented method according to claim 9, wherein the force sensor is included within the compression paddle.

11. The computer-implemented method according to claim 9, wherein the corrective action includes determining and displaying a movement score on a display device.

12. The computer-implemented method according to claim 9, wherein the corrective action includes displaying an alert on a display device indicating that the movement threshold has been exceeded.

13. The computer-implemented method according to claim 9, wherein the corrective action includes triggering a visual indicator of an imaging system.

14. The computer-implemented method according to claim 9, wherein determining whether deleting the first image from the plurality of images exceeds the image removal threshold further comprises identifying each image of the plurality of images associated with a movement signal exceeding the movement threshold.

15. The computer-implemented method according to claim 14, wherein determining whether deleting the first image from the plurality of images exceeds the image removal threshold comprises determining that deleting the first image would not exceed the image removal threshold; and
the corrective action comprises deleting the first image from the plurality of images.

16. The computer-implemented method according to claim 15, wherein determining whether deleting the first image from the plurality of images exceeds the image removal threshold comprises determining that deleting the first image would exceed the image removal threshold; and
the corrective action comprises cancelling the imaging sequence.

17. An article comprising a non-transitory computer-readable storage medium including instructions that, when executed by a processor, cause a system to perform the computer-implemented method of claim 9.

* * * * *